US005250440A

United States Patent [19]

Kelln et al.

[11] Patent Number: 5,250,440
[45] Date of Patent: Oct. 5, 1993

[54] CUVETTE DELIVERY MODULE AND TURNTABLE FOR A CHEMICAL ANALYZER

[75] Inventors: Norman Kelln, Spokane; Bruce Weyrauch, Newman Lake; James Clark; Dan Cutler, both of Spokane, all of Wash.

[73] Assignee: Schiapparelli Biosystems, Inc., Fairfield, N.J.

[21] Appl. No.: 916,179

[22] Filed: Jul. 16, 1992

[51] Int. Cl.⁵ .................... G01N 35/02; G01N 21/00
[52] U.S. Cl. ............................ 436/48; 436/45; 436/43; 436/165; 356/246; 422/58; 422/63; 422/64; 422/82.05; 422/82.09; 422/102; 422/104
[58] Field of Search ............ 422/58, 64, 63, 102, 422/82.05, 82.09, 104; 436/165, 43, 45, 48; 356/246

[56] References Cited

U.S. PATENT DOCUMENTS

| 4,634,575 | 1/1987 | Kawakami et al. | 23/230 R |
| 4,764,342 | 8/1988 | Kelln et al. | 422/72 |
| 5,055,262 | 10/1991 | Sakagami | 422/64 |
| 5,071,625 | 12/1991 | Kelln et al. | 422/72 |
| 5,096,672 | 3/1992 | Tervamaki et al. | 422/102 |
| 5,175,086 | 12/1992 | Takekawa et al. | 435/7.92 |

FOREIGN PATENT DOCUMENTS 2131168  6/1984  United Kingdom .
8800704  1/1988  World Int. Prop. O. .

Primary Examiner—James C. Housel
Assistant Examiner—N. Bhat
Attorney, Agent, or Firm—Wells, St. John, Roberts, Gregory & Matkin

[57] ABSTRACT

The cuvette delivery apparatus for an automatic chemical analyzer includes a magazine that stores multiple stacks of substantially rectangular cuvettes. A ram outwardly adjacent to the magazine moves an exposed cuvette from a selected stack into an awaiting compartment of a turntable. Random access is provided to all stacks within the magazine. A mechanical follower monitors the selected stack and provides stack information for updating of cuvette inventory.

20 Claims, 18 Drawing Sheets

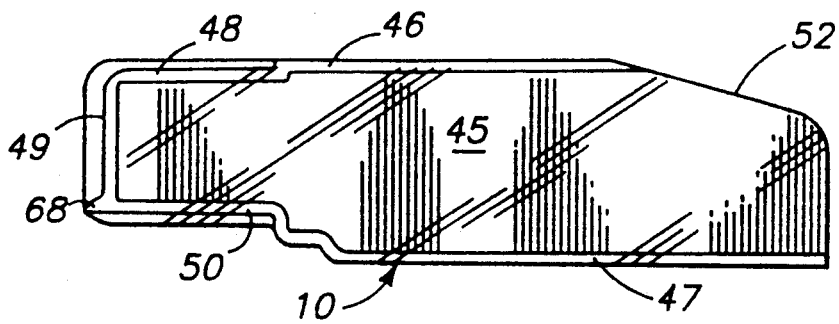
_FIG 6_
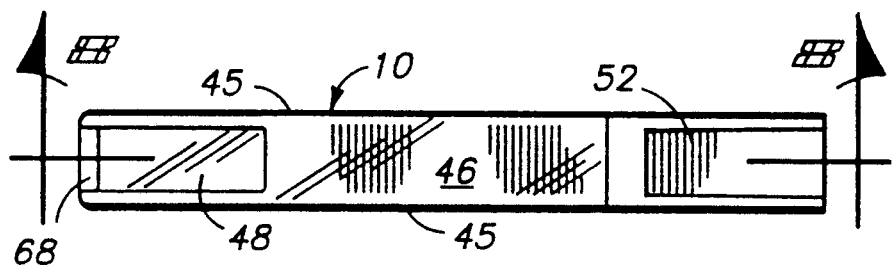
_FIG 7_
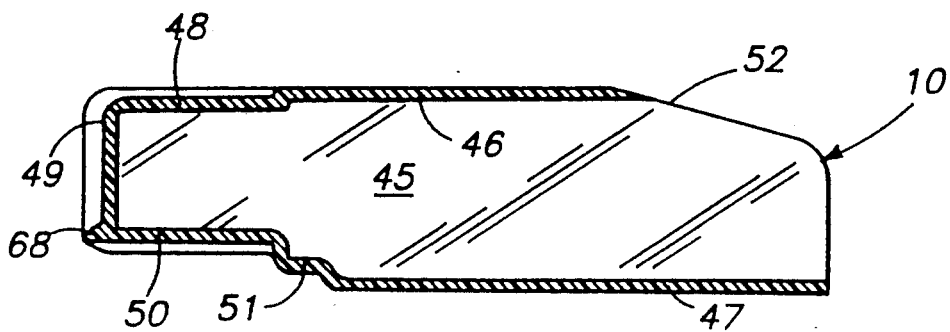
_FIG 8_

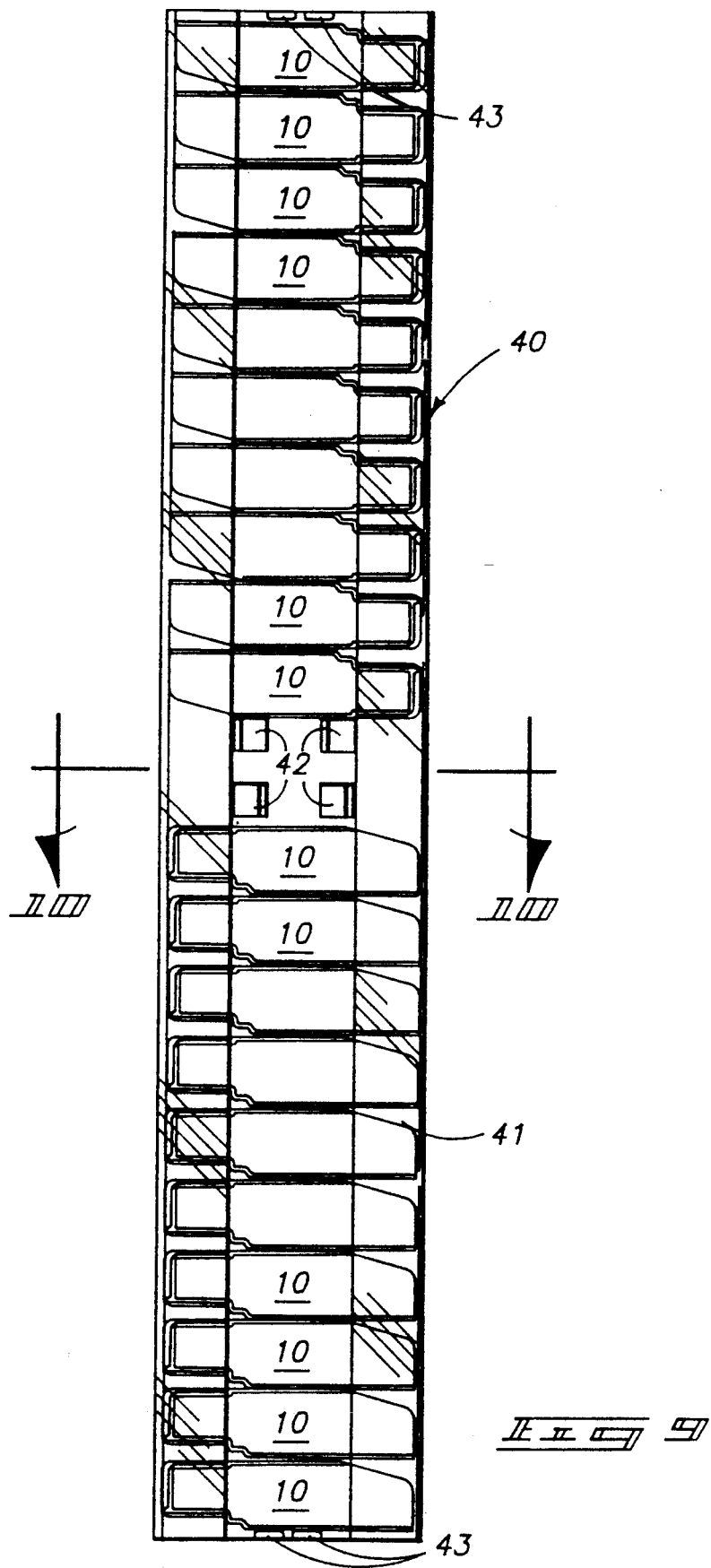

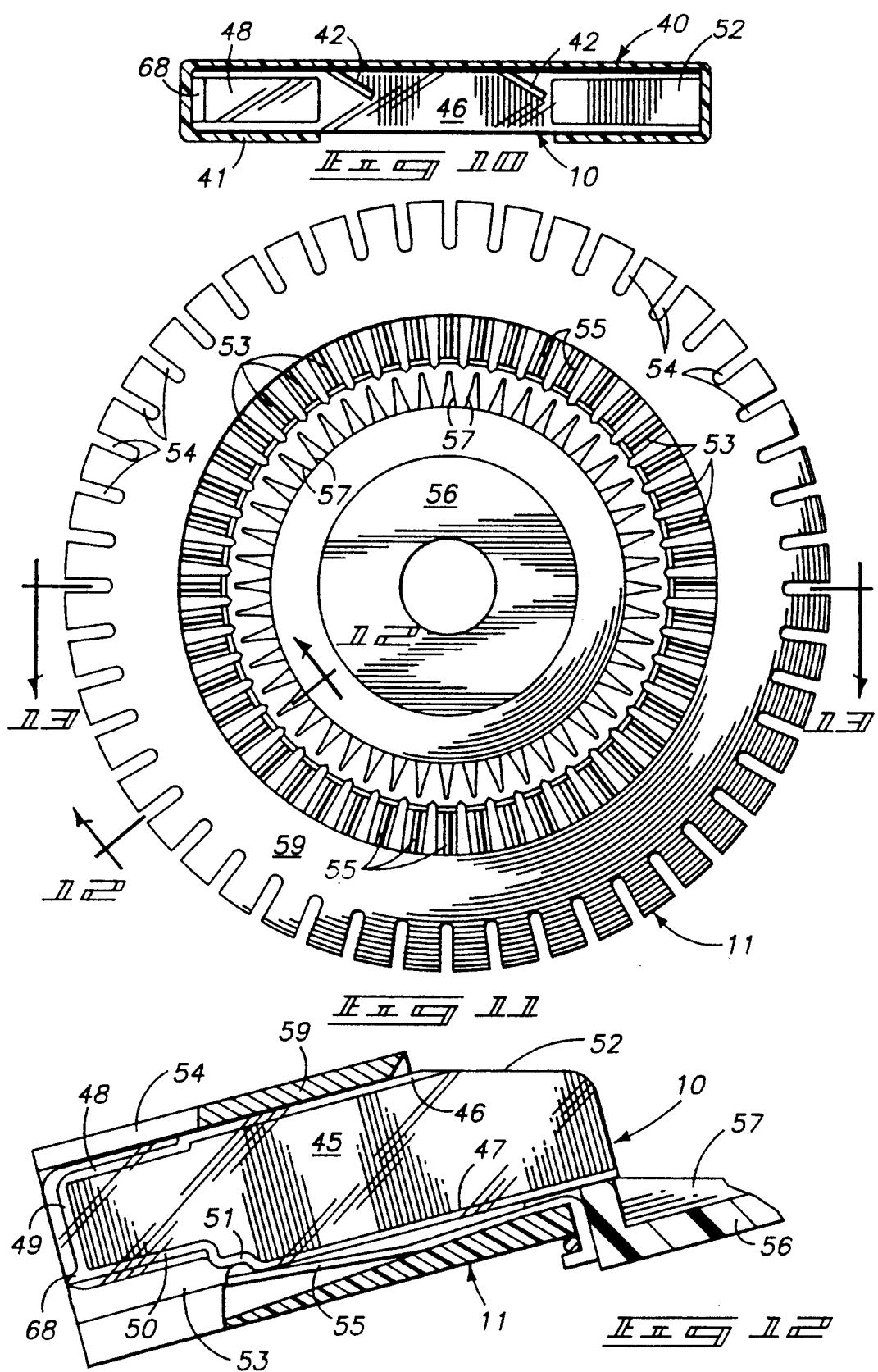

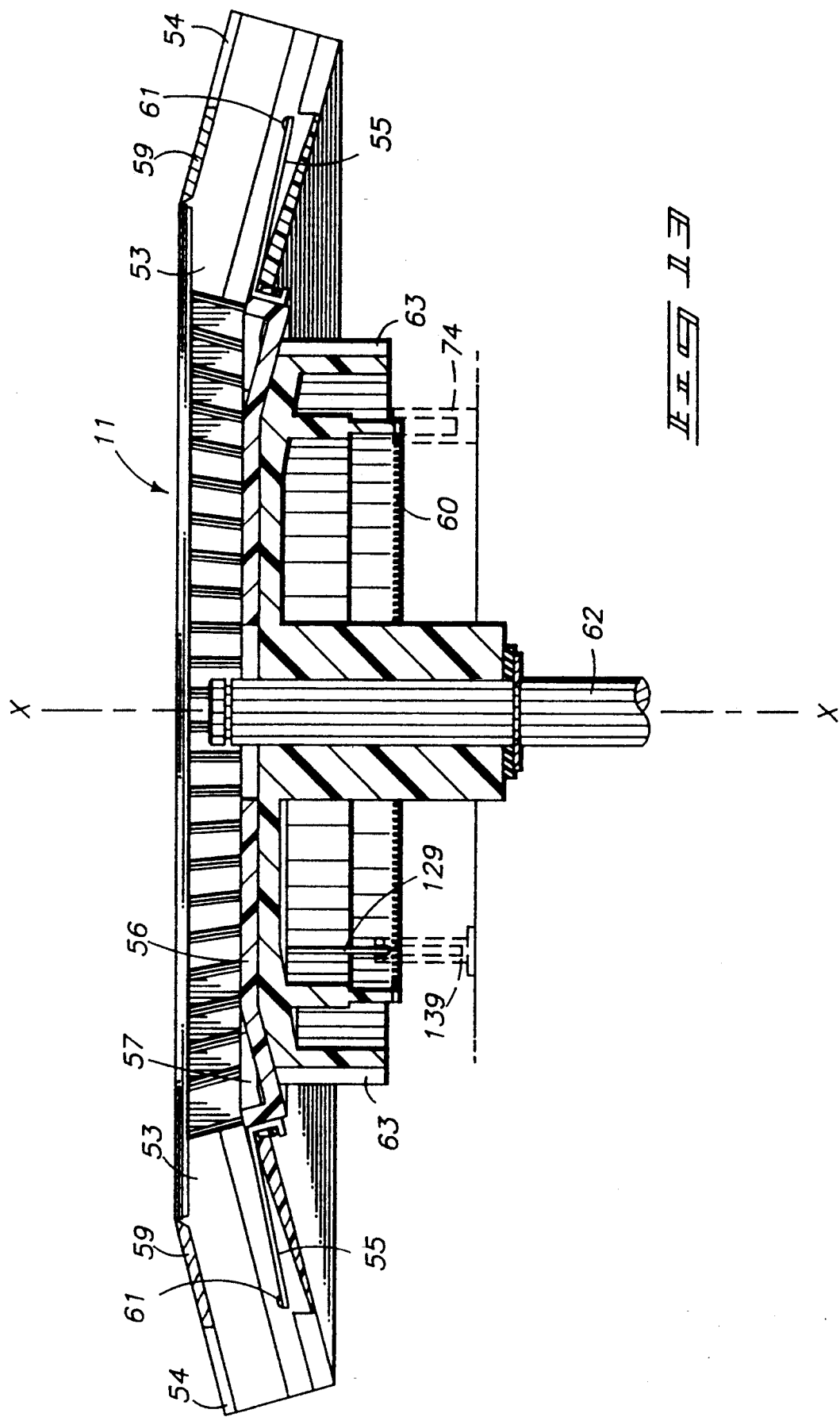

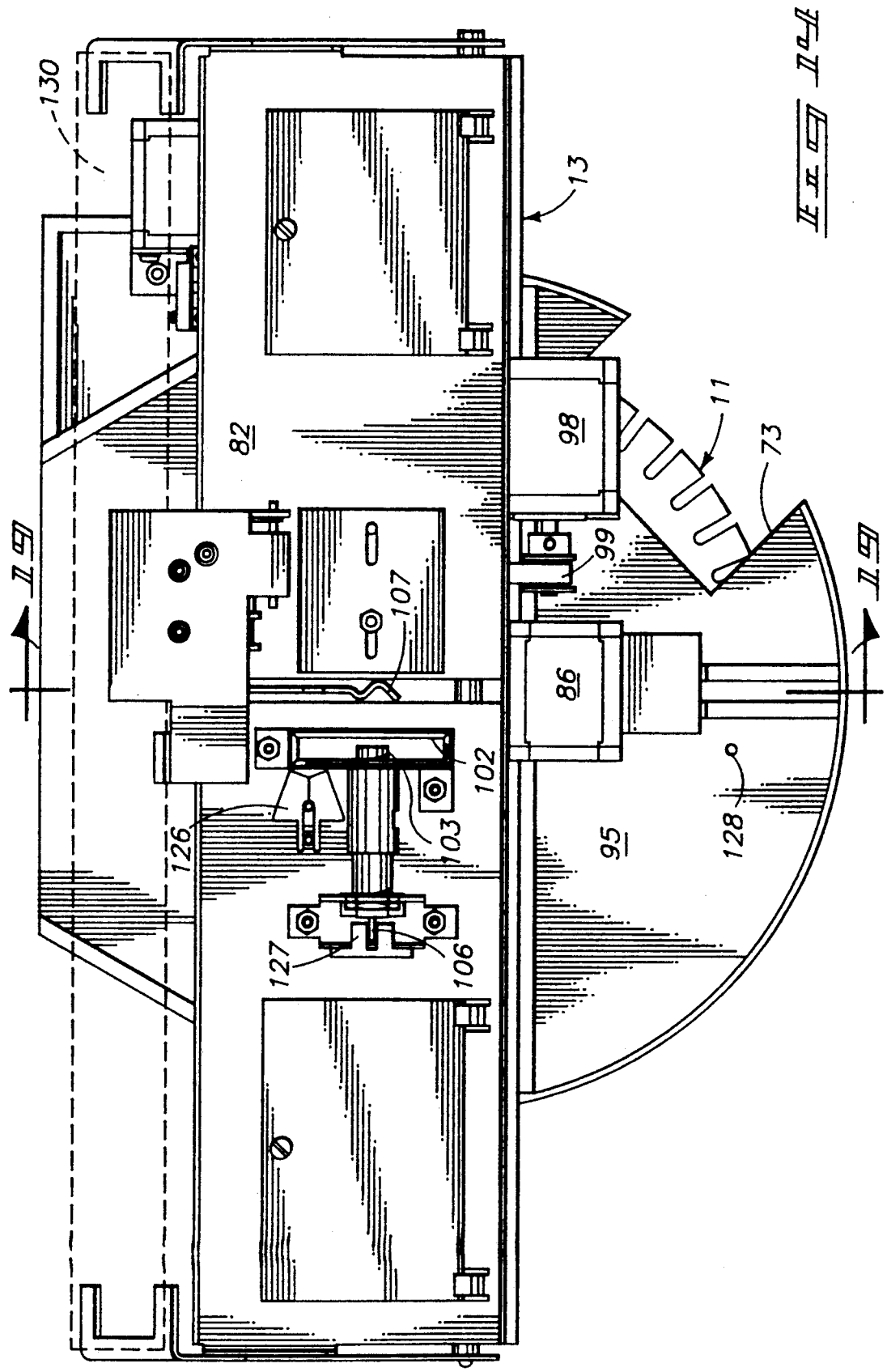

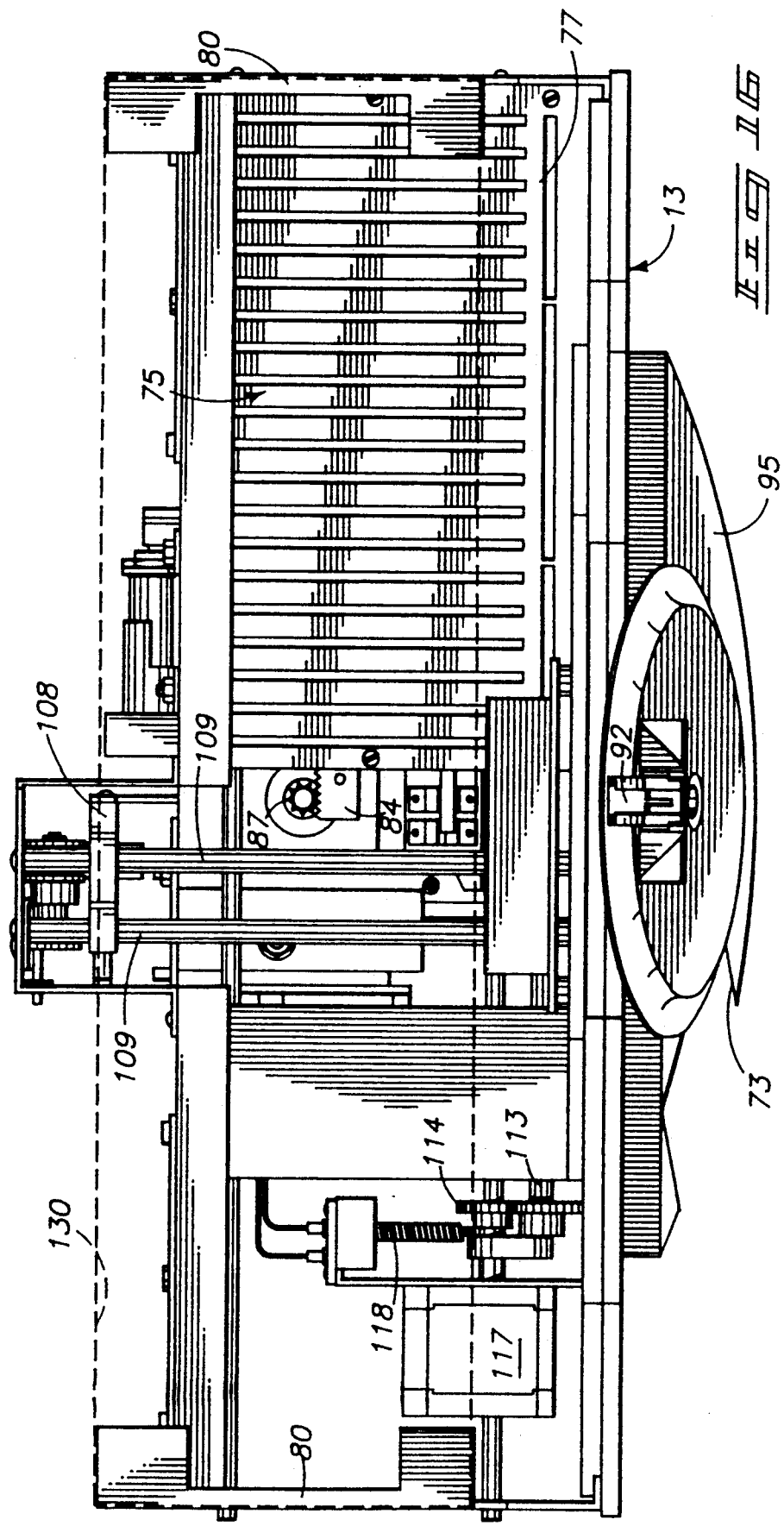

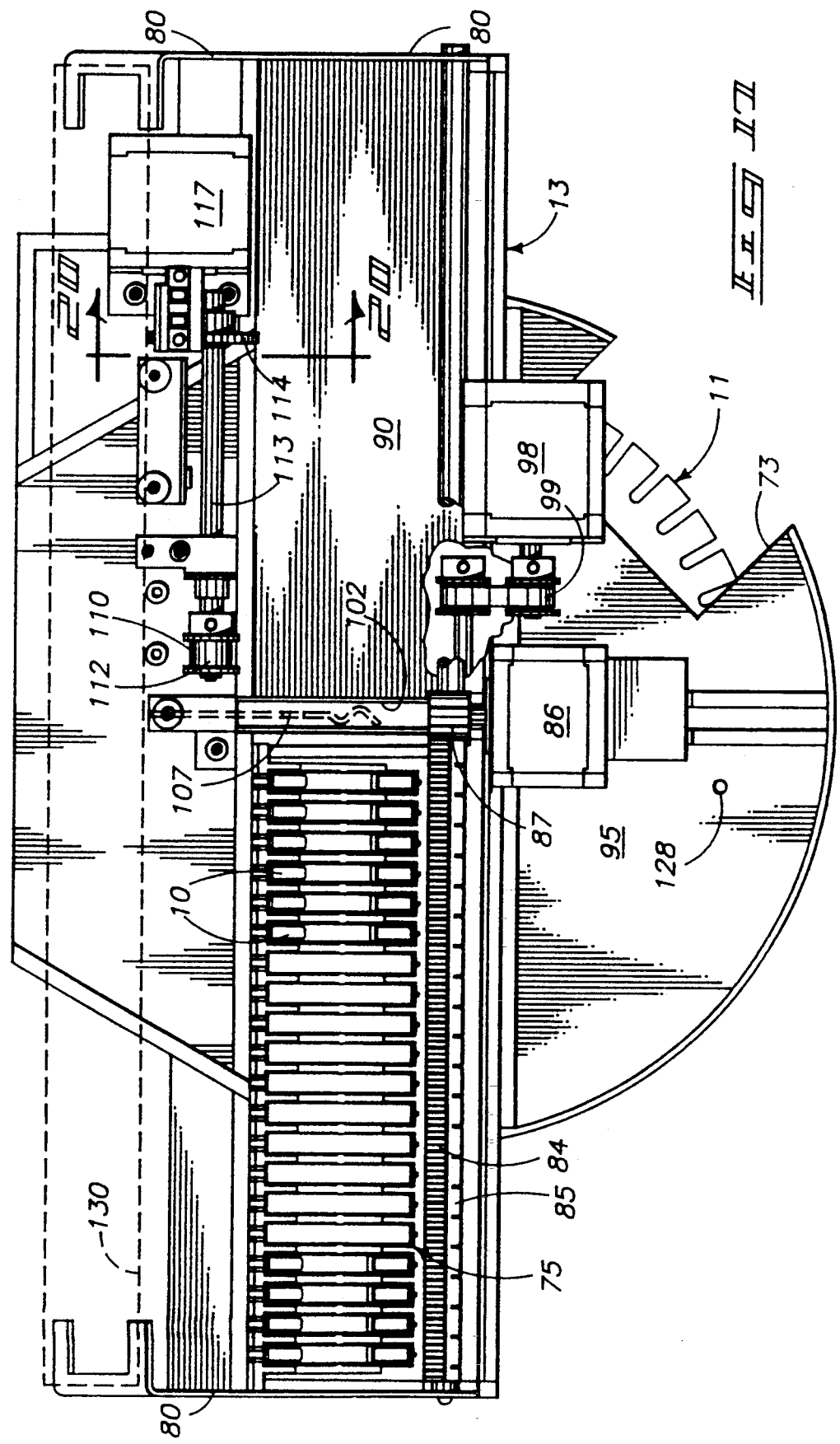

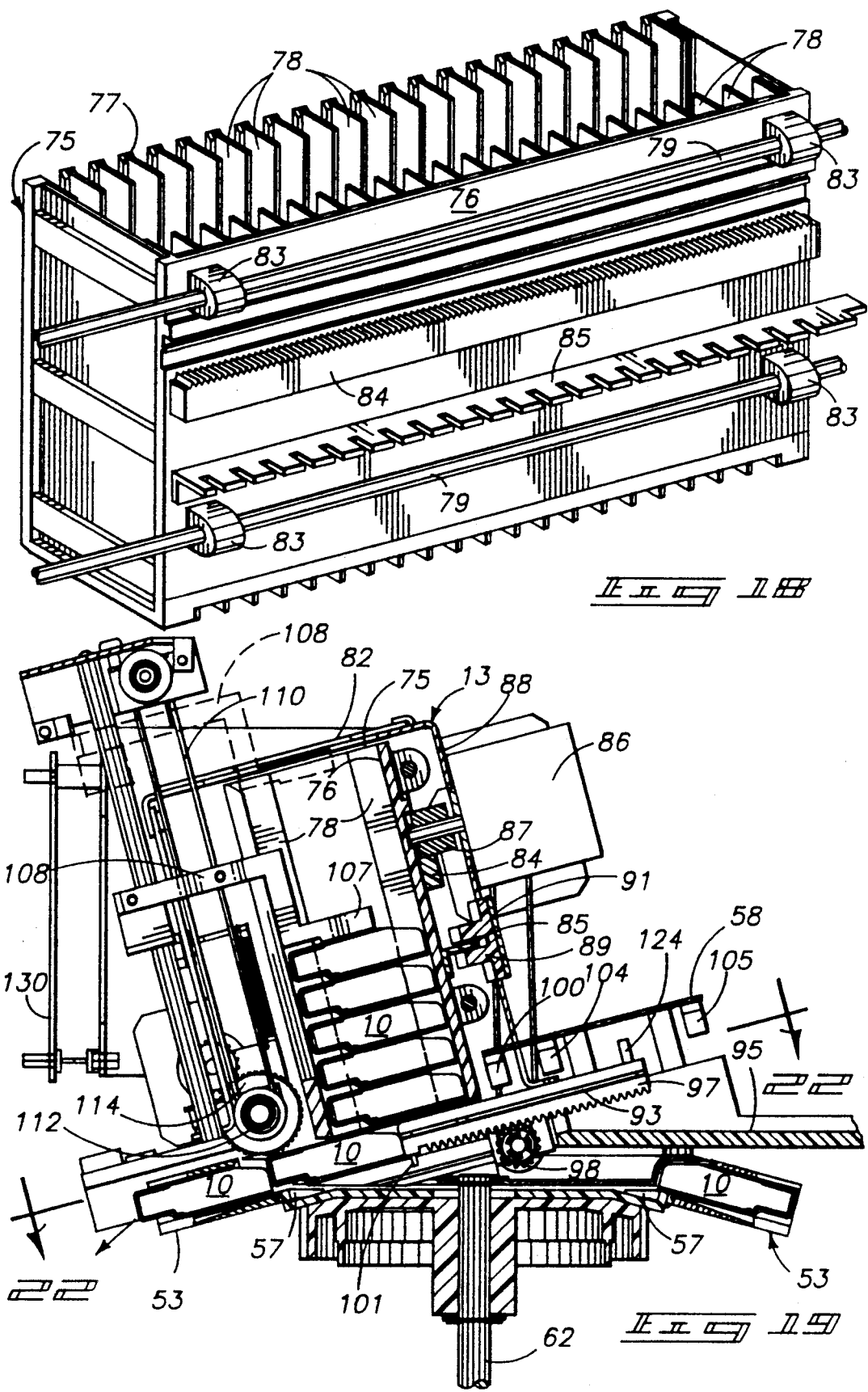

| TURNTABLE 11 | STATIONARY | MIX | ACCEL-ERATE | SPIN | | | DECEL-ERATE |
|---|---|---|---|---|---|---|---|
| PROBE ARM 17 | DISPENSE FLUID | WASH (SHORT) | | | | | |
| MAGAZINE 75 | INSERT CUVETTE | | | | | | |
| OPTICAL SYSTEM 14 | MOVE FILTER OUT | TRANSMIT DATA | | | ABSORBANCE READINGS | MOVE FILTER IN | FLOUR-ESCENCE READINGS |

FIG. 25

CUVETTE DELIVERY MODULE AND TURNTABLE FOR A CHEMICAL ANALYZER

TECHNICAL FIELD

This disclosure pertains to a cuvette delivery apparatus for a clinical chemistry analyzer for testing of patient samples, such as blood or urine, in disposable cuvettes. It generally relates to automatic chemical analyzers for qualitative and quantitative analyses of tested samples on a rotating turntable. More specifically, it pertains to automatic equipment for storing such cuvettes and randomly delivering them on an individual basis to the awaiting turntable.

BACKGROUND OF THE INVENTION

Automated analyzers have been developed for biochemical analysis of patient samples, such as whole blood, serum, urine, plasma and cerebral spinal fluid. Most such equipment available today is complicated to operate, large in size and high in cost.

The operation of such equipment is technically complicated. It typically requires specialized operators to be available at all times, with commensurate personnel expenses being encountered. It is usually designed for use by large laboratories serving a wide geographic area or by a large medical facility. These existing analyzers carry out tests in a defined sequence of operations designed for efficient, high volume usage.

Such large scale capacity is not always required, particularly in smaller medical clinics where large volumes of blood samples are not encountered on a daily basis. The present chemical analyzer was developed to meet the practical needs of smaller medical settings. It is designed as a desk-top unit that can be operated without specialized laboratory training. Its throughput is adequate for meeting typical clinical applications.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements.

To obtain large volumes of tests, conventional laboratory analyzers are programmed to conduct test procedures in a fixed sequence of events. While predetermined test sequences are practical in high volume chemical analyzer applications, there is a need for more flexible operation when sealing such test procedures to meet the needs of smaller medical facilities.

The present invention provides testing flexibility by permitting random access to each cuvette on a test turntable. It is therefore not necessary for the instrument to sequence through any predetermined processing steps-the controlling software can tailor the required steps to the tests currently requisitioned. This permits a greater number of tests to be conducted while using a minimum number of containers, cuvettes and reagent bottles. The software controls the sequencing of tests based upon predetermined priority schedules, rather than defined test sequences dictated by the nature of the tests being conducted.

Increased versatility is also provided in the present chemical analyzer by providing the capability of inserting pre-loaded reagents within cuvettes fed to a dispensing magazine that directs them to the turntable. Flexibility is further enhanced by providing random access to a plurality of stacks of incoming cuvettes, some of which can be preloaded and some of which can be empty. This provides the capability of random access to prepackaged chemistry involving powdered or solid reagents to supplement the liquid reagents available on the sample/reagent tray.

Disposable cuvettes are provided automatically within the analyzer by a cuvette dispenser. Reloading of the cuvettes into a dispensing magazine included in the chemistry instrument is physically organized to meet the supply needs of the instrument with minimum cuvette handling by the operator.

A reaction turntable is capable of handling a maximum of 48 cuvettes at any given time. Both absorbance and fluorescence polarization tests can be carried out with respect to selected cuvettes through use of a single optical system.

Further details concerning the system will be evident from the following description.

BRIEF DESCRIPTION OF THE DRAWINGS

The preferred embodiment of the invention is illustrated in the accompanying drawings, in which:

FIG. 6 is a side elevation view of a cuvette;

FIG. 7 is a top view;

FIG. 8 is a sectional elevation view taken along line 8—8 in FIG. 7;

FIG. 9 is a front elevation view of a loaded cuvette cartridge;

FIG. 10 is a transverse sectional view through a loaded cartridge as seen along line 10—10 in FIG. 9;

FIG. 11 is a plan view of the cuvette turntable;

FIG. 12 is an enlarged sectional view taken along line 12—12 in FIG. 11;

FIG. 13 is a transverse sectional view through the turntable as seen along line 13—13 in FIG. 11;

FIG. 14 is a plan view of the cuvette delivery module;

FIG. 16 is a similar rear elevation view, the turntable being removed;

FIG. 17 is a plan of the delivery module with its cover removed;

FIG. 18 is a perspective view of the cuvette magazine;

FIG. 19 is a transverse vertical sectional view of the delivery module as seen along line 19—19 in FIG. 14;

FIG. 25 is a timing diagram for the instrument components.

DETAILED DESCRIPTION OF THE PREFERRED EMBODIMENT

Figure 1:
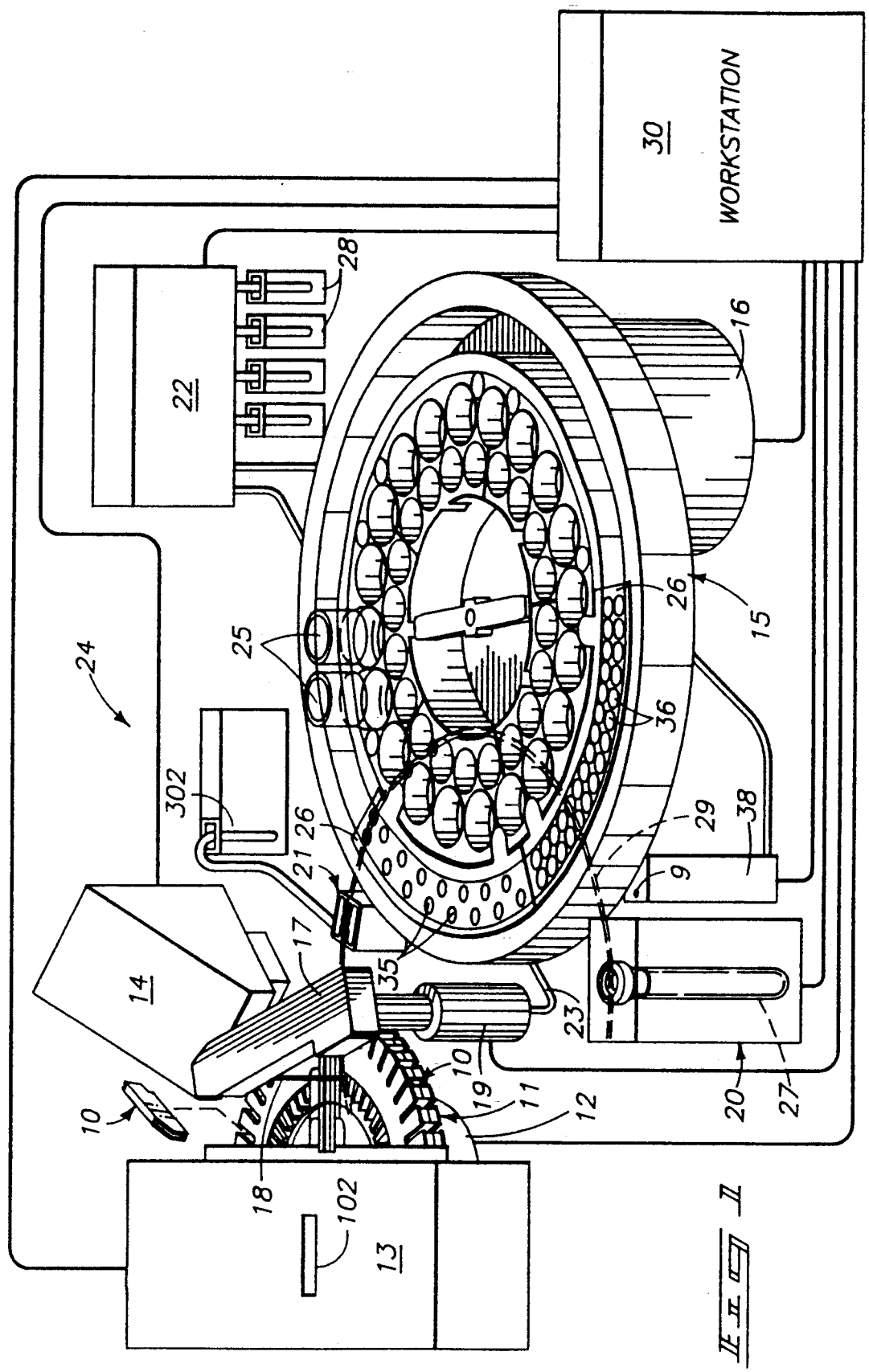
FIG. 1 is a diagrammatic perspective view of the principal components in the analyzer.

This disclosure of the invention is submitted in furtherance of the constitutional purposes of the U.S. Patent Laws "to promote the progress of science and useful arts" (Article 1, Section 8).

System Overview

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2-5). It separates along a peripheral parting line 37 defining a lower supporting base 33 and an upper hinged cover 34.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors-one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidently impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
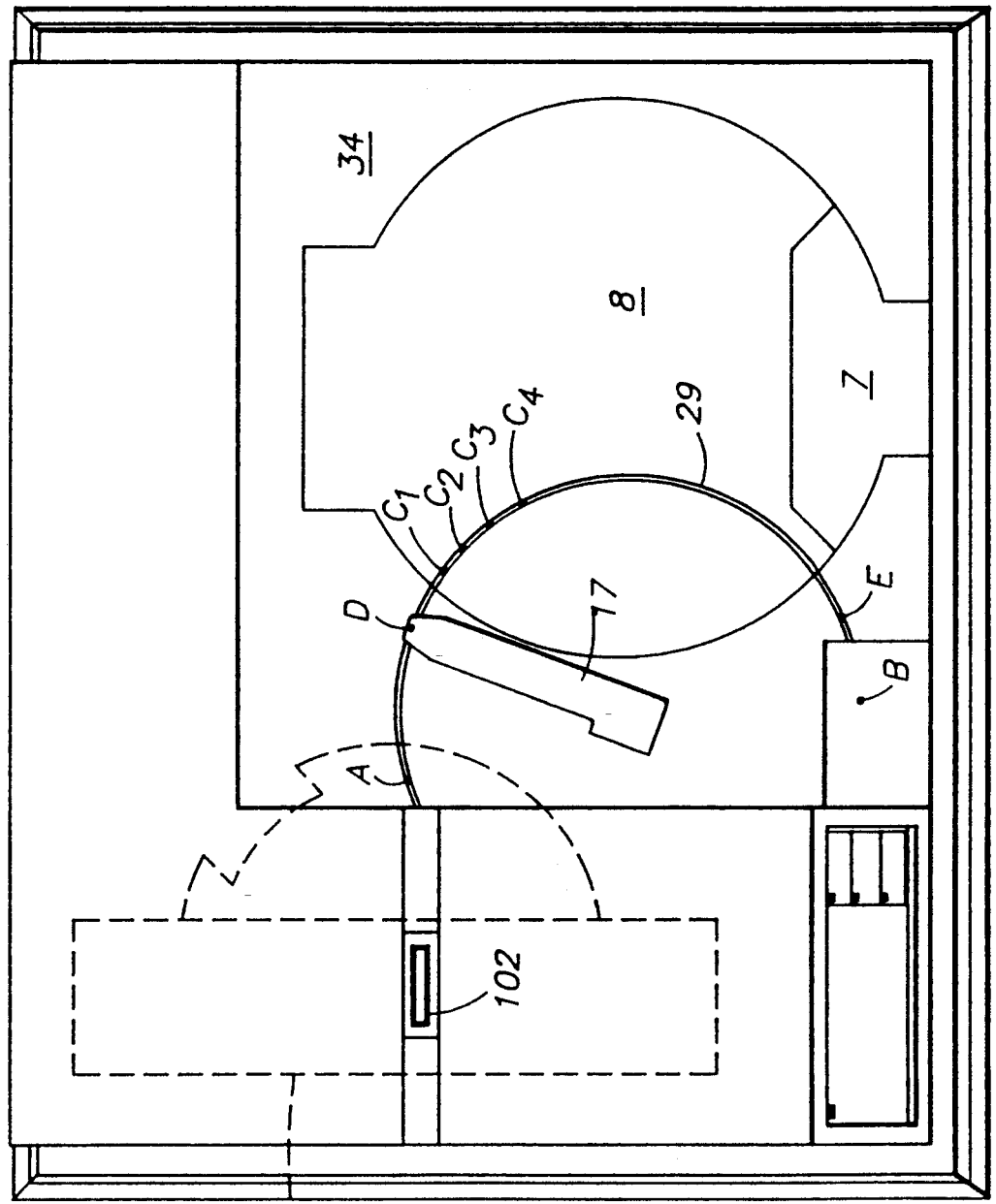
FIG. 3 is a plan view of the chemical instrument enclosure.
Figure 4:
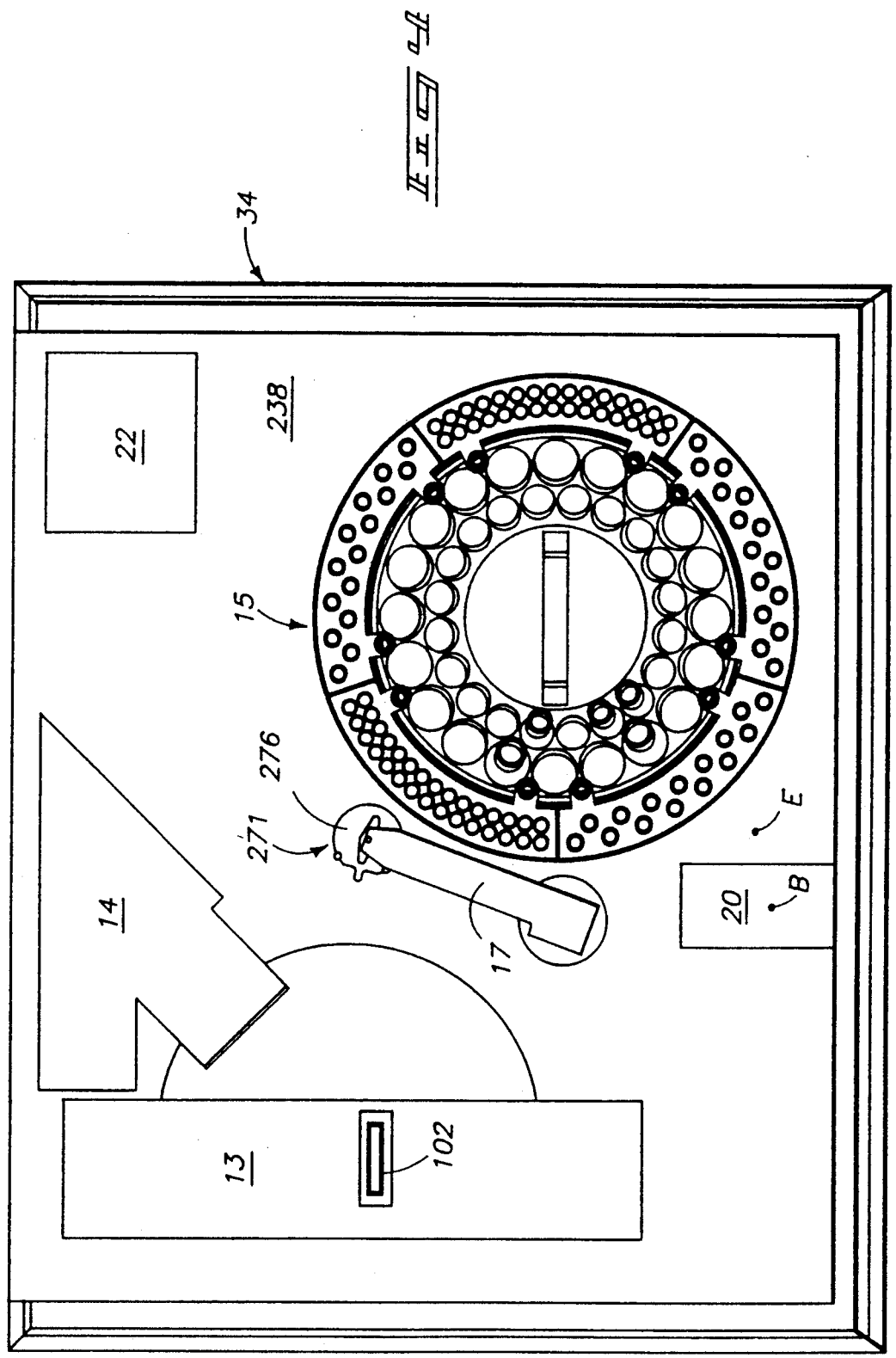
FIG. 4 is a plan view of the chemical instrument enclosure with the cover removed.
Figure 5:
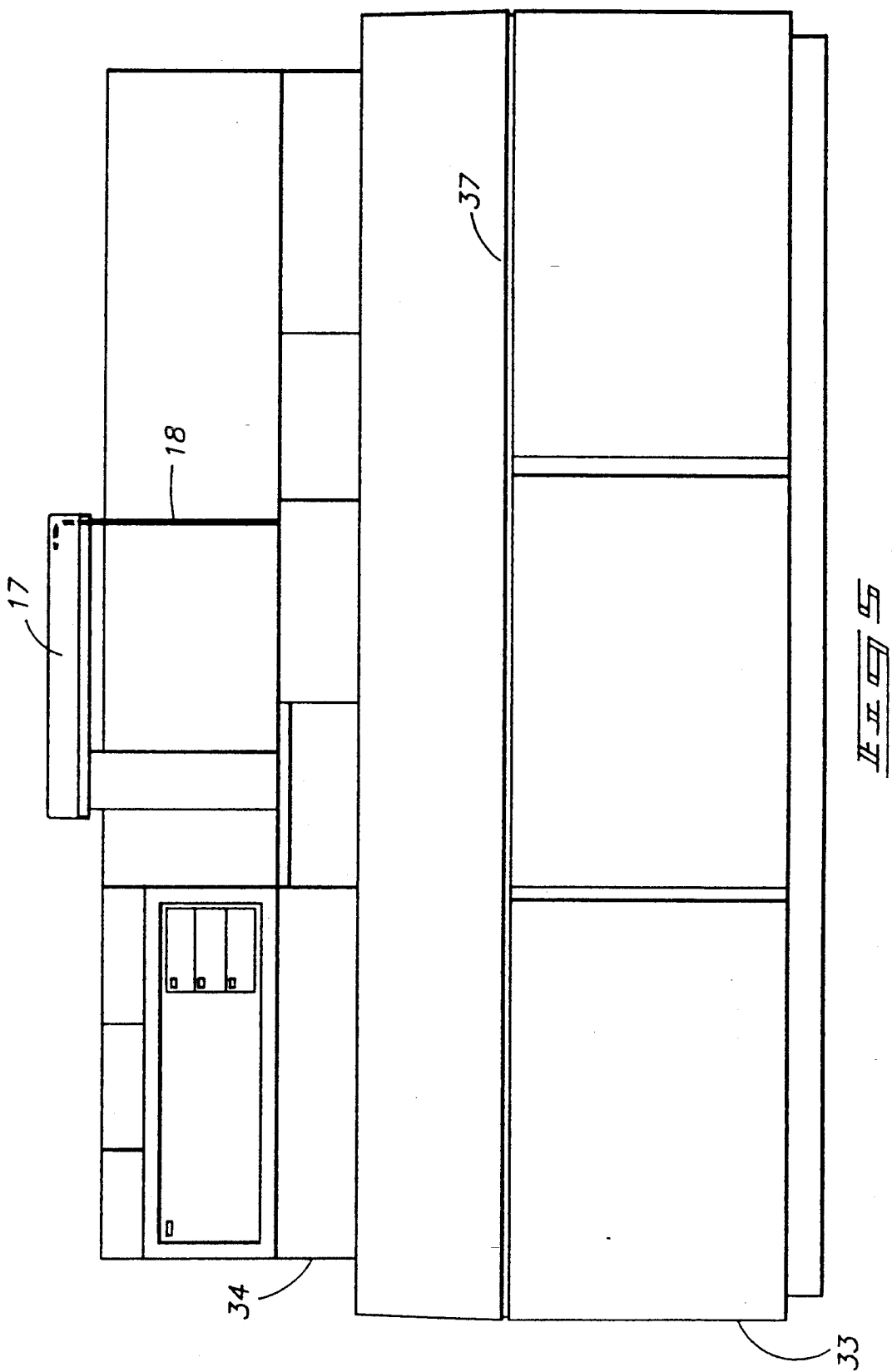
FIG. 5 is a front elevation view of the enclosure.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the area of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20. The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Cuvettes

The disposable cuvettes 10 designed for use in turntable 11 are illustrated in detail in FIGS. 6-8. A complementary cartridge 40 for handling and storing the cuvettes is shown in FIGS. 9 and 10.

Cuvettes 10 are molded from a suitable transparent rigid plastic material that is liquid impervious and inert to the liquids which they are to contain. The cross-sectional configuration of each cuvette is rectangular.

Each cuvette 10 includes two identical side walls 45 having parallel top and bottom edges. The straight top and bottom edges along each side wall 45 longitudinally overlap one another to facilitate stacking of the cuvettes in abutting parallel positions. Side walls 45 are transversely joined by parallel spaced top and bottom walls 46 and 47.

One end of each cuvette 10, termed its "upper end", includes an opening 52 between the end edges of the side walls 45. Opening 52 provides access to the interior of cuvette 10 for receipt of liquids. The edges of side walls 45 that form the opening 52 include angular edges intersecting the straight top edges of the respective side walls 45. The angular edges assume horizontal orientations when positioned in turntable 11 (FIG. 12). The end edges along the opening 52 are perpendicular to the top and bottom walls 46 and 47. In the case of cuvettes that are pre-loaded with reagents or other materials prior to usage in the chemistry instrument 24, opening 52 can optionally be sealed by a suitable film or other cover (not shown) capable of being pierced by the descending tip of pipette 18.

The opposite end of each cuvette 10, termed its "lower end", includes perpendicular optical surfaces for transmission of light in conjunction with operation of the optical system 14. These surfaces comprise top, end and bottom optical surfaces 48, 49 and 50, respectively. Each optical surface area is slightly recessed inwardly from the outer edges of side walls 45 to protect the optical surfaces from abrasion or contact during handling.

The lower end of each cuvette 10 also is provided with a transverse protruding wall 68 extending across the two side walls 45. Wall 68 provides a continuous transverse surface for abutment of the upper end of an adjacent cuvette 10 when one cuvette pushes another into position within turntable 11.

A small downwardly-facing recess 51 is provided within the bottom wall 47 of each cuvette 10 adjacent to the inner end of lower optical surface 50. The recess 51 serves as a detent in conjunction with a spring-biased enlargement (see FIG. 12) that yieldably holds cuvette 10 within a receiving compartment on the turntable 11.

The cuvettes are preferably packaged within elongated disposable cartridges 40 (see FIGS. 9 and 10). The parallel stacked cuvettes 10 face oppositely at the respective ends of cartridge 40. Which is designed for insertion into the open slots of a receiving cuvette magazine 75 detailed in FIG. 18.

The cuvette cartridge 40 is formed from a C-shaped channel 41 having interior surfaces complementary to the exterior shape and size of the individual cuvettes 10. Cartridge 40 can be formed from any suitable stiff, resilient plastic sheet or can be extruded in the shape generally illustrated in FIGS. 9 and 10. Its purpose is to facilitate handling and storage of the large quantities of cuvettes 10 required by each chemistry instrument 24 and to expedite manual entry of cuvettes 10 into the storage magazine 75.

Cuvettes 10 fit transversely within the elongated channel 41 in abutting parallel positions within two groups. Each group of cuvettes 10 at the respective ends of cartridge 40 equals a full stack of cuvettes within the receiving magazine 75 as described below. Two pairs of inwardly bent stops 42 near the center of cartridge 40 limit inward motion of cuvettes along the length of the magazine. Outward movement of cuvettes at each end of the cartridge 40 is resisted by smaller end stops 43 bent inwardly in the path of cuvettes 10 as they exit the cartridge 40.

Turntable

Turntable 11 is generally detailed in FIGS. 11–13. It comprises a circular, radially-slotted wheel rotatably mounted about a vertical axis X—X (FIG. 13). The outer periphery of the turntable 11 presents a series of equiangularly spaced radial compartments 53. Each compartment 53 individually receives a cuvette 10 in the manner shown in FIG. 12.

Each compartment 53 comprises a radial slot having an interior cross-sectional shape and size that is complementary to the exterior cross-sectional shape and size of a cuvette 10. The compartments 53 are arranged about turntable 11 at an oblique angle such that the angular upper edge of each cuvette opening will be oriented horizontally and perpendicular to the axis X—X (see FIG. 12). The oblique nature of each compartment also positions the optical end of each cuvette 10 at a lower elevation than opening 52 so that liquids will be contained within each cuvette without spilling, even when the turntable 11 is stationary.

An axial slot 54 intersects each compartment 53 across its outer end. Slots 54 extend through the upper and lower surfaces of the turntable 11. They provide light access to the optical surfaces 48–50 of cuvettes 10. Slots 54 permit passage of light through the individual cuvettes 10 and are used in conjunction with operation of the optical system 14 to facilitate photometric testing of cuvette contents while within the turntable 11.

The cuvettes are yieldably held within the radial compartments 53 by spring 55 (FIGS. 12, 13). The outer ends 61 of the longitudinal springs 55 are enlarged to enable them to fit within the recesses 51 formed in the cuvettes 10. The spring ends 61 constitute yieldable detents that radially limit outward movement of each cuvette 10 relative to the turntable 11.

Springs 55 also serve as interior supports within compartments 53. They yieldably maintain the top walls 46 of cuvettes 10 in engagement with the upper inside surfaces of the compartments 53. The cover 59 about turntable 11 is fabricated of an electrically conductive plastic material. Springs 55 maintain firm surface-to-surface contact between the top wall 46 of each cuvette 10 and the interior surface of cover 59. This provides effective heat transfer to each cuvette to minimize the time required to warm it in preparation for receipt of a test sample. The metal cover 59 can be heated as the turntable 11 is rotated, using an adjacent stationary source of controlled heat (not shown).

Cuvettes 10 held within the turntable 11 are individually accessible and open for reception of samples and reagents as required by requisitioned assays. Liquids are introduced through the openings 52 of the respective cuvettes 10 by operation of probe arm 17 and pipette 18 at the previously-identified cuvette access station A. All incubation of samples involved in an assay occurs within cuvettes 10 in the turntable 11.

The upper surface of the supporting central plate 56 on turntable 11 is provided with a plurality of tapered radial guide surfaces 57. Surfaces 57 are centered between each radial compartment 53 and are obliquely aligned with the respective compartments 53. They are utilized to accurately index turntable 11 during reception of incoming cuvettes, as will be described in conjunction with the interaction between the cuvette dispenser module 13 and turntable 11.

As can be seen in FIG. 12, the turntable 11 holds cuvettes 10 in elevationally tilted radial positions with their openings 52 exposed for reception of liquid materials. At the same time, their optical surfaces 48, 49 and 50 are exposed through slots 54 for transmission of light as required by operation of optical system 14.

Turntable 11 is rotatably supported about a stationary vertical shaft 62 (FIG. 13) fixed to the supporting framework of the chemistry instrument 24. It is rotated by peripheral gear teeth 63 that are drivingly engaged with a motor-driven gear (not shown) operatively powered by motor 12.

Indexing of turntable 11 is accomplished by a circular slotted rim 60 that rotates between a light sensor 74 on the framework of the chemistry instrument. A rotational "home" position is defined be a depending flag 129 and a second sensor 139.

Cuvette Delivery Module

The cuvette delivery module 13 is located across the left hand end of the enclosure for the chemistry instrument, as shown in FIG. 3. A plan view of the cuvette delivery module 13 is illustrated in FIG. 14. It is further illustrated in FIGS. 15–23. It overlies turntable 11 at an oblique angle aligned with the compartments 53 (see FIG. 19).

Cuvette delivery module 13 provides automated storage for a plurality of stacks of cuvettes 10 delivered to it from manually-inserted cartridges 40. The cuvettes 10 are stored in parallel upright stacks within a longitudinally shiftable magazine 75. The magazine 75 is separately illustrated at FIG. 18.

Cuvettes discharged from a selected stack within magazine 75 are individually inserted into a selected compartment 53 on the turntable 11. Insertion of a cuvette 10 into a turntable compartment 53 in turn ejects the cuvette 10 previously within it (see FIG. 19). Ejected cuvettes can be temporarily stored within a rigid or flexible container (not shown) on the framework of the chemistry instrument 24. The receiving container should be upwardly open, allowing the ejected cuvettes 11 to drop freely into it from the turntable 11.

Magazine 75 is capable of randomly accessing the individual cuvettes exposed at the lower end of any one of its multiple stacks. This capability is of particular value when stacks of pre-loaded cuvettes containing differing reagents are stored in magazine 75. When simply using empty stored cuvettes 10, the stacks of cuvettes within magazine 75 will be accessed in sequence, with all of the cuvettes in a stack being delivered to the turntable 11 before a subsequent stack is used.

Magazine 75 comprises an elongated, rectangular, box-like structure including transversely spaced side walls 76 and 77. Walls 76 and 77 support opposed inner upright walls 78. The inner walls 78 define a series of upright slots, each slot having a width and thickness complementary in size to the corresponding dimensions of a cuvette cartridge 40. The slots are therefore sized to complement the exterior length and thickness of the stacked cuvettes 10. The stacked cuvettes 10 fit loosely within the receiving slots. They are fed downwardly within the slots for eventual individual discharge at the bottom of each stack.

The stationary support for the movable magazine 75 is fixed within the hinged cover 34 of the exterior enclosure for the chemistry instrument 24. It includes a base 81 and attached vertical end walls 80. An arcuate hood 95 is integral with base 81 and covers most of the protruding portions of turntable 11. It is interrupted about a portion of its periphery by an opening 73 to expose an arcuate section of the turntable 11, as can be seen in FIGS. 14-17.

Hood 95 has an open aperture 128 formed through it. Aperture 128 is positioned at the cuvette access station A shown in FIG. 3. Pipette 18 can freely pass through aperture 128 to locate its lower end or tip within the opening 52 at the upper end of an indexed cuvette 10 on turntable 11 for discharge of fluid.

Magazine 75 is covered by a top wall 82 arranged between the end walls 80 in close proximity to the upper ends of the magazine slots. The top wall 82, which can include removable access panels, prevents cuvettes from falling from the magazine when the cover 34 of the enclosure is lifted about its hinges.

Magazine 75 is longitudinally guided on a pair of horizontal rods 79 extending between the end walls 80. Side wall 76 of magazine 75 is provided with spaced bushings 83 that slidably support magazine 75 along the horizontal rods 79.

An exterior rack 84 along the outer surface of the magazine wall 76 imparts longitudinal motion to it. The longitudinal position of magazine 75 relative to the module base 81 is controlled by operation of a stepper motor 86 that drives magazine 75 through a gear 87 in mesh with rack 84 (see FIG. 19). Motor 86 is fixed to an upstanding side plate 88 at the center of module 13.

A longitudinal indexing strip 85 along the wall 76 of magazine 75 is periodically slotted to facilitate optical indexing of magazine 75 relative to its supporting structure within the cuvette delivery module 13. Plate 88 mounts a light sensor 89 that straddles the indexing strip 85 to detect the positions of the slots in indexing strip 85. Associated electronic components for the sensor 89 can be provided on a circuitboard shown at 91.

Cuvettes 10 located within magazine 75 freely rest on a smooth planar upper surface 90 presented across the module base 81. The surface 90 is interrupted only by a central transverse slot 92 through which the lowermost cuvette 10 within a select stack aligned above it within magazine 75 is delivered for entry into a compartment 53 in turntable 11 (See FIGS. 19, 22 and 23).

Slot 92 is closed or opened by movement of a flush-mounted ram 93 slidably guided within it. Ram 93 is transversely guided within base 81 for movement along slot 92. It moves between an extended inner position, an outer position, and a cuvette inserting position.

Figure 22:
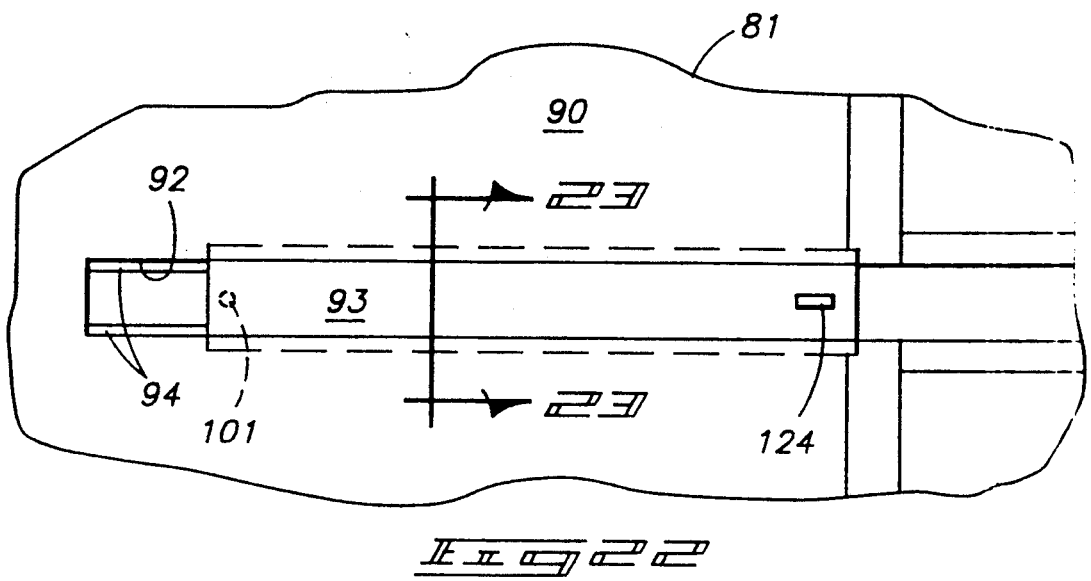
FIG. 22 is an enlarged fragmentary view taken along the cuvette-receiving slot as seen along line 22—22 in FIG. 19.
Figure 23:
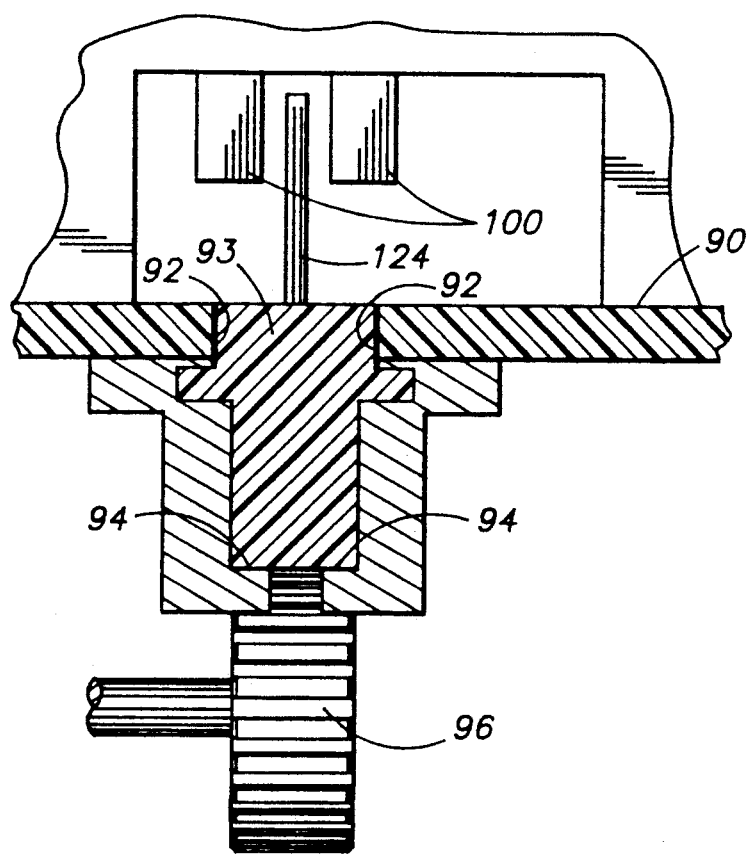
FIG. 23 is a sectional view taken along line 23—23 in FIG. 22.

Incoming cuvettes 10 within slot 92 are vertically supported on opposed transverse ledges 94 within the open slot 92 (FIGS. 22, 23). They can then be pushed into an indexed compartment 53 on the turntable 11 by reciprocation of ram 93.

The ram 93 is illustrated in FIG. 19 at a position where it partially closes the opening presented by slot 92 and is pushing a cuvette 10 into a turntable compartment 53. Ram 93 also is movable inwardly along the empty slot 92 before it allows a cuvette 10 to drop within slot 92, to cause a pin 101 at its underside to wedge between paired tapered guide surfaces 57 on turntable 11. This mechanically indexes turntable about axis X—X for subsequent accurate reception of a cuvette 10 within compartment 53. The retracted position of ram 93 leaves slot 92 fully open to receive cuvette 10 within it.

Figure 15:
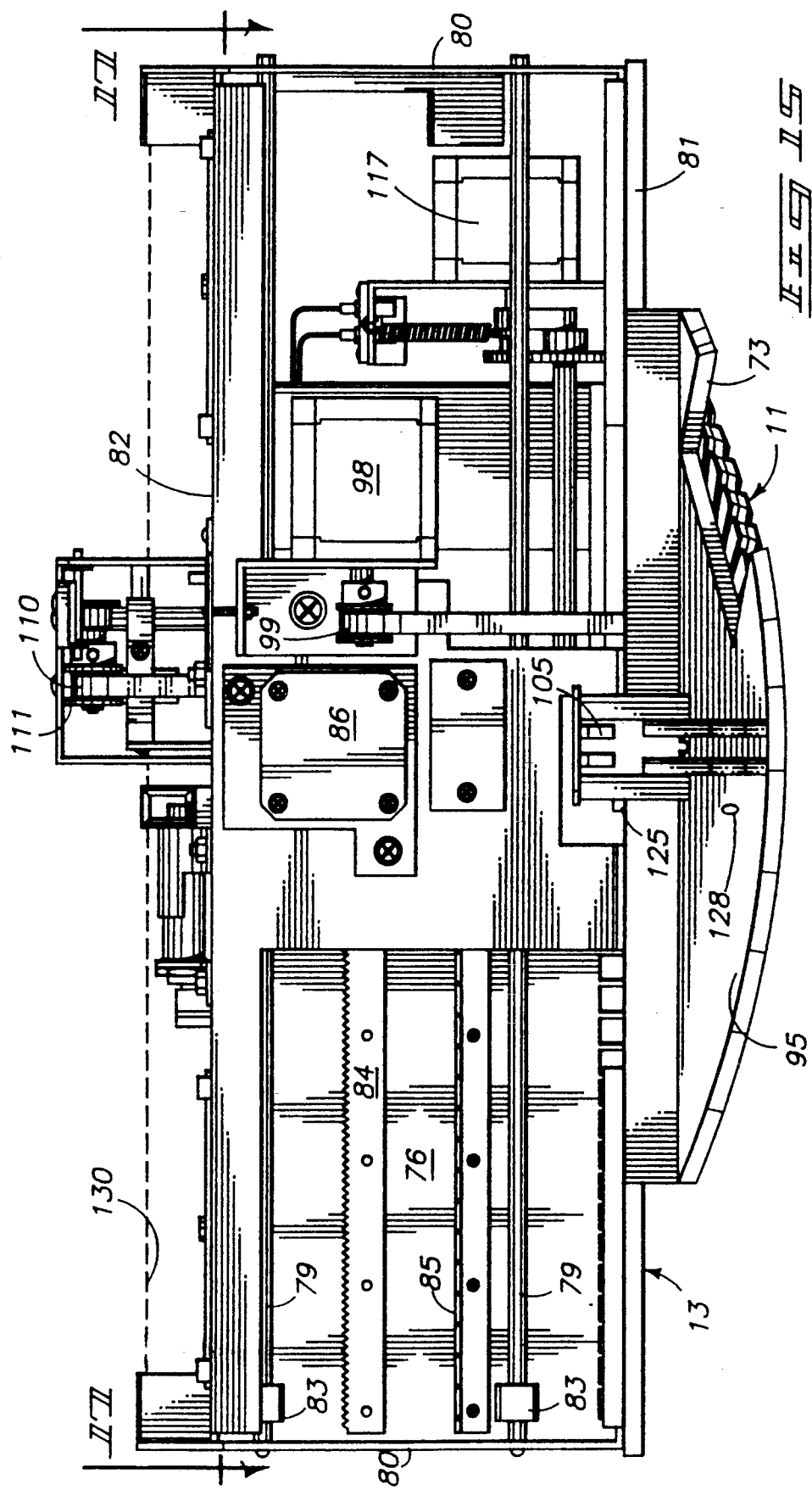
FIG. 15 is a front elevation view taken parallel to the side wall of the delivery module.
Figures 20, 21:
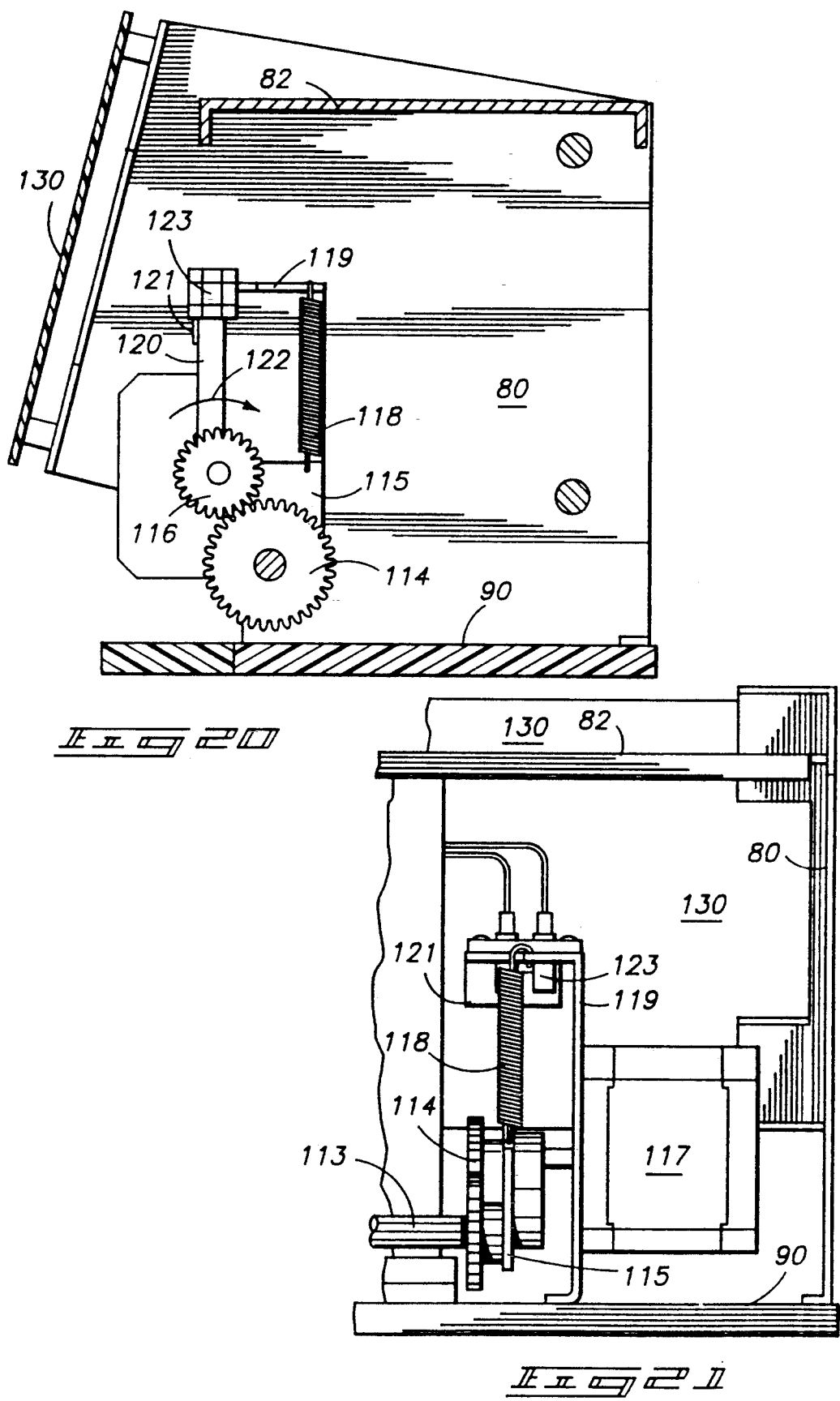
FIG. 20 is a transverse sectional view taken along line 20—20 in FIG. 17.
FIG. 21 is a side view of the elements shown in FIG. 20.

The ram 93 is powered by a rotatable gear 96 that meshes with a downwardly facing rack 97 formed along the bottom of ram 93 (FIGS. 19 and 23). Gear 96 is powered by a motor 98 on side plate 88 through interconnecting pulleys and a timing belt 99 as shown in FIG. 15.

Three limits of motion of ram 93 are detected by light sensors 100, 104 and 105, respectively, which detect the position of an upwardly protruding tab 124 at the outer end of ram 93. Associated electronic components for the photocells are mounted on a circuitboard 58.

The normal inoperative position of ram 93 is set with tab 124 at intermediate sensor 104. The sequence of movement by ram 93 involves three distinct phases. After turntable 11 has been angularly indexed by motor 12 to receive a cuvette 11, ram 93 is moved inwardly from the position shown in FIG. 22 until tab 124 is detected by sensor 100. This causes pin 101 to wedge between a pair of tapered guide surfaces 57 to assure that a turntable compartment 53 is accurately aligned with the ram 93 for reception of a cuvette 10. Ram 93 next fully retracts until tab 124 is detected by sensor 105. This allows a waiting cuvette to fall through the open slot 92 and rest on ledges 94. Ram 93 then moves inwardly until tab 124 is again detected by sensor 100, thus inserting a new cuvette into the compartment 53 and causing the incoming cuvette to simultaneously eject the preceding cuvette from the turntable compartment. The downward motion of each stack of cuvettes 10 is monitored by a vertically movable follower 107, described in detail below.

Each end of the complementary cuvette cartridges 40 holds a complete stack of cuvettes. The inventory system for the magazine 75 is based upon a manual loading protocol whereby individual stacks of cuvettes 10 are to be replenished only after they have been totally depleted.

Figure 2:
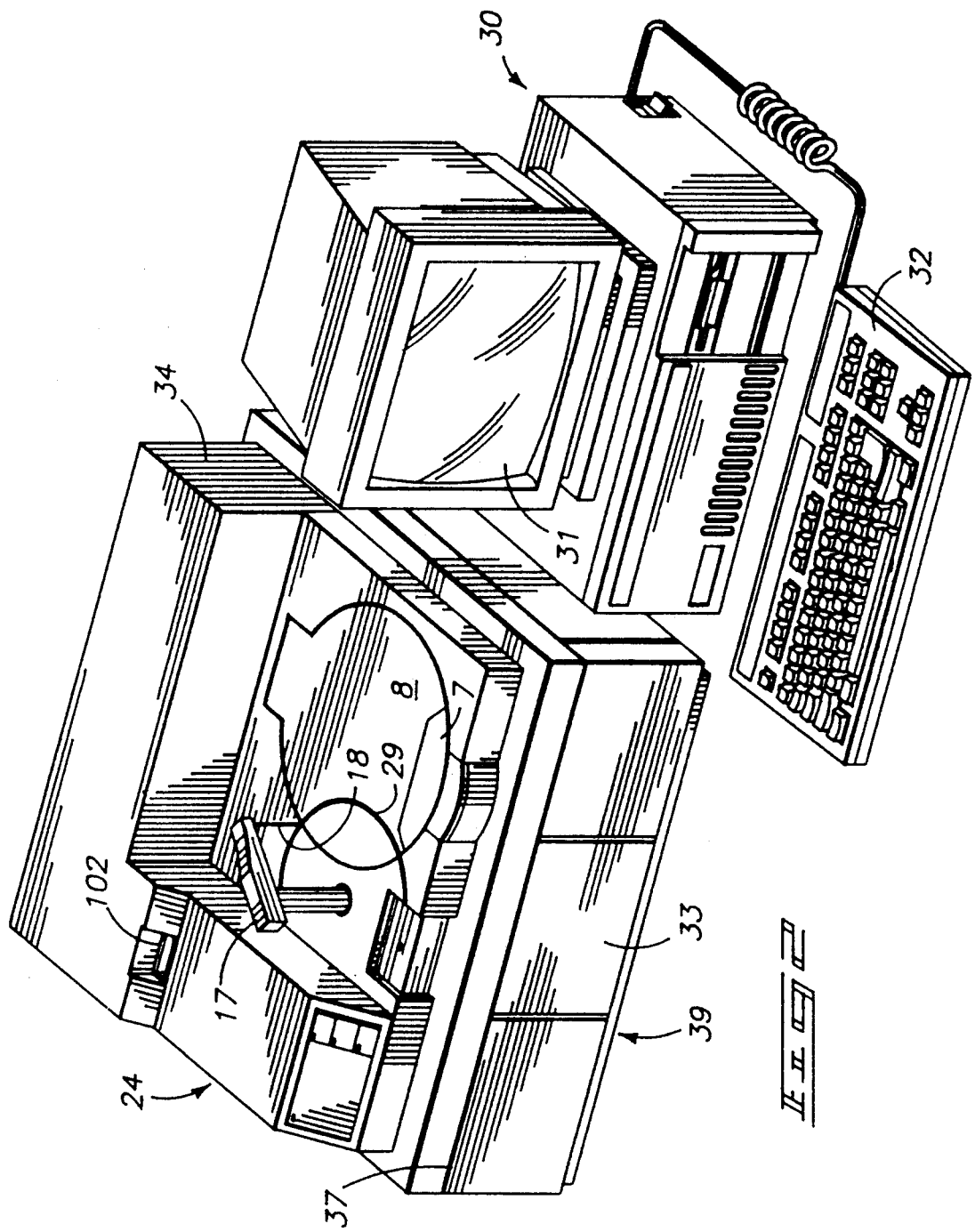
FIG. 2 is a perspective view of the analyzer.

One end of a cuvette cartridge 40 can be manually inserted into the cuvette delivery module 13 through a slotted guide 102 formed through the enclosure cover 34 (see FIGS. 2 and 3). The guide 102 is transversely intersected by a solenoid-controlled stripper 103 shown in FIG. 14 that blocks entrance of cuvettes until they are required. Retraction of the normally-extended stripper 103 is enabled only when a photocell assembly 126 trained through a slot in guide 102 detects the presence of a cuvette cartridge 40. Actual retraction of stripper 103 is controlled by software instructions from workstation 30, which is programmed to permit refilling of magazine 75 only when a magazine slot under the guide 102 is empty. Retraction of stripper 103 is verified by a photocell assembly 127 mounted on top wall assembly 82, which straddles an extension pin 106 integral with stripper 103.

The elevation of photocell assembly 126 is lower than that of the stripper 103. Thus, the incoming end of cartridge 40 cannot pass the stripper and operate photocell assembly 104 if it is facing improperly within the slotted guide 102. Its lower edge will first abut the upper surface of stripper 103. This provides a mechanical interlock to assure that cartridge 40 and cuvettes 10 within are not inserted into magazine 75 in a backwardly-facing orientation.

If oriented properly within the slotted guide 102, an incoming cuvette cartridge 40 can be manually pushed through the aligned slot within magazine 75 until its lower end abuts the planar upper surface 90. A photocell sensor 125 directed across surface 90 then detects the fully inserted position of the cartridge 40 and causes the stripper 103 to be extended to its normal position across guide 102. The shaft of stripper 103 then fits between the open legs of the cuvette cartridge 40 in the area between its center stops 42.

Cartridge 40 is removed from within magazine 75 by manually lifting it. The extended end of stripper 103 intersects the location of cuvettes 10 within the legs of the C-shaped channel 41 and prevents their upward movement, thereby causing them to remain in a stacked arrangement within the selected vertical slot of the receiving magazine 75.

Inventorying of cuvettes by workstation 30 is based upon an assumption that a full stack of cuvettes 10 will be supplied to magazine 75 during each loading sequence. The controlling software can maintain information as to the slots within the magazine 75 that contain full stacks of cuvettes 10. It is therefore necessary only to monitor the partial stack of cuvettes being delivered to the turntable 11 during current use of the chemistry instrument 24 and to physically measure the height of each stack of cuvettes within magazine 75 at machine startup to provide complete inventory information at all times. These functions are accomplished by a vertically movable follower 107.

The follower 107 is slidably guided by a supporting bracket 108 fitted about two upright rods 109. This support arrangement for follower 107 is best seen in FIG. 16. Follower 107 can be moved vertically between a normal elevated position clear of magazine 75, as shown in dashed lines at the top of FIG. 19, and a lowered position at which it rests upon the uppermost cuvette 10 in a selected stack within magazine 75, as also illustrated in FIG. 19.

Follower 107 and bracket 108 are moved vertically by means of a timing belt 110. Bracket 108 is clamped to one flight of the belt 110, which is entrained over upper and lower pulleys 111, 112. Follower 107 remains in a horizontal position at all times, thereby resisting any tendency of the stacked cuvettes 10 beneath it to assume an angular orientation within the confining walls of the magazine 75.

Engagement of follower 107 with the uppermost cuvette 10 in a stack is detected by the resulting torsional forces exerted on pulley 112 through interconnecting belt 110. Pulley 112 is mounted to an extended shaft 113 leading to a gear 114 at the opposite end of shaft 113 (see FIGS. 17, 20 and 21). Gear 114 is rotatably supported on a bracket 115, which in turn is pivotally supported about the axis of a meshing gear 116 powered directly by a driving stepper motor 117.

Bracket 115 is biased to a normal position wherein the axis of shaft 113 is parallel to the axis of driving gear 116. The biasing forces on bracket 115 are provided by a tension spring 118 connected between bracket 115 and a fixed plate 119 which mounts the motor 117. In this normal position, an extension arm 120 that is integral with bracket 115 abuts a side ledge 121 on the plate 119. However, when follower 107 engages a cuvette at the top of a stack, the resulting torsional forces on gear 114 will cause the bracket 115 to pivot slightly in the direction shown by arrow 122 in FIG. 20. This torsional movement can be detected by a photocell sensor 123 that straddles arm 120. Sensor 123 is fixed to plate 119.

A printed circuitboard 130 is provided across the remaining side of the cuvette delivery module 13 and mounts the electronic components associated with it. The details of the printed circuitboard 130 are not shown. It is to be understood that the electronic controls for the various motors, sensors, and solenoids will be interconnected in the usual manner so as to perform the functions of the module as described herein.

Controller System

Figure 24:
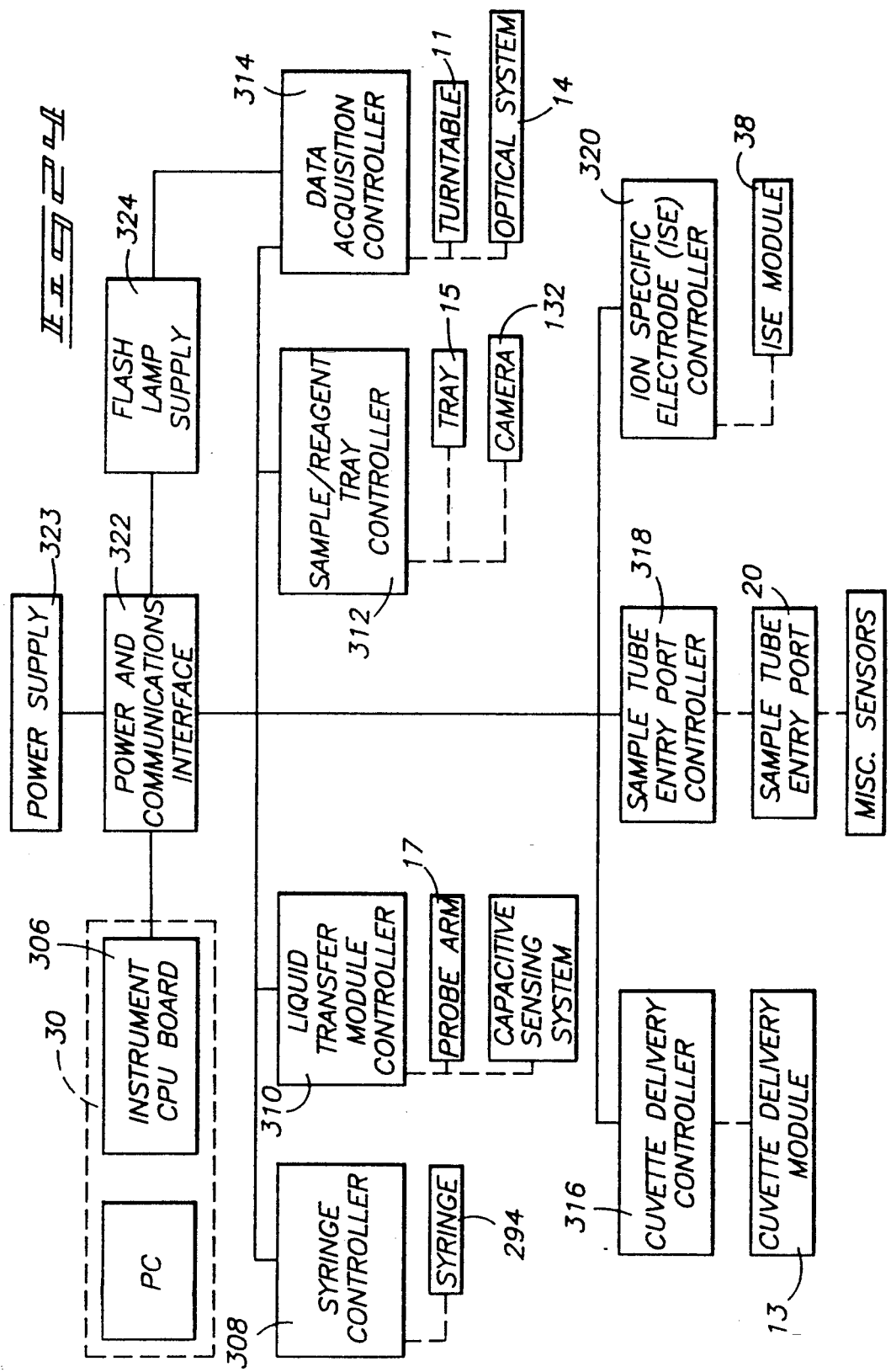
FIG. 24 is a block diagram of the instrument controllers.

The computerized controller system for the various modules included within the chemistry instrument 24 is diagrammatically illustrated in FIG. 24. The control circuitry shown in FIG. 24 is that associated with a single chemistry instrument 24. Where two chemistry instruments 24 are utilized in a single installation, the illustrated components (other than workstation 30) will be duplicated for each instrument.

Scheduling of physical operations to be carried out in the chemistry instrument 24 is controlled by an instrument central processing unit (CPU) circuitboard 306. The instrument CPU board 306, located physically within workstation 30, is programmed to schedule the randomly available operations of the chemistry instrument modules as permitted by the status of its affected modular components and as required by a requisitioned assay. Board 306 includes a suitable microprocessor and memory devices for storing logic and scheduling programs required to operate the chemistry instrument.

The control system for each chemistry instrument 24 includes a distributed family of controller microprocessors located within its various modules. In the preferred embodiment shown in FIG. 24, there are seven microprocessor controllers associated with operation of the instrument components. Their respective operational functions and associated modular components are as follows:

Syringe Controller 308—directly controls operation of syringe motor for syringe 294. Controller 308 monitors the linear position of the syringe piston by means of signals supplied by an optical sensor 300. It also operates the valves associated with syringe 294.

Liquid Transfer Module Controller 310—moves probe arm 17 both vertically and angularly through use of operator 19. Photocell sensors associated with probe arm 17 and operator 19 provide signals indicative of the preset vertical and angular positions of probe arm 17. Controller 310 also maintains desired liquid temperatures for liquids in the tubing arranged along the probe arm 17 that leads to pipette 18 through monitored operation of heating element 375. It additionally controls operation of the capacitive sensing system shown.

Sample/Reagent Tray Controller 312—operates motor 16 to selectively position sample/reagent tray 15 about its axis. It monitors sensors to accurately index tray 15 at a selected angular position for pipette access to a selected container. It also controls operation of the reagent bottle label readers. The sample/reagent tray controller 312 is further responsible for maintaining suitable reagent temperatures through selective operation of cooling elements (not shown) associated with tray 15 and is connected to a sensor which selectively detects the presence of cups 35 within a ring segment 26.

Data Acquisition Controller 314—Controls rotation and indexing of turntable 11 through operation of motor 12. Indexing information is supplied to it from sensors 74 and 139 adjacent to the turntable 11 (FIG. 13). Controller 314 also operates the elements included within optical system 14 and relays resulting absorbance and fluorescence data for tested samples.

Cuvette Delivery Controller 316—Operates the components of cuvette delivery module 13 through control of motors 86, 98, and 117, and stripper 103. It further provides temperature controls for heating and cooling devices (not shown) associated with turntable 11 for maintaining desired reaction temperatures during its operation.

Sample Tube Entry Port Controller 318—Governs operation of sample tube entry port 20. It receives signals from sensors that detect the presence of each draw tube as it is manually inserted into the chemistry instrument 124. Controller 318 coordinates movement of the components within sample tube entry port 20 with movement of probe arm 17. In addition, it controls operation of a scanner that reads information from bar coded labels or other optical data on each incoming draw tube. Controller 318 further monitors miscellaneous activities required for effective use of the chemistry instrument 24, including conditions of the diluent supply within container rack 28 and the status of waste liquid container 302, segment access port 7, tray access cover 8, various access doors, and the cuvette disposal container.

Ion Specific Electrode (ISE) Controller 320—Controls operation of the ISE module 38 to selectively test samples for the presence of electrolytes such as sodium, potassium, chloride, lithium and calcium. The operational functions of this controller are dictated by conventional operation of the ISE module 38 and are well known to those skilled in such technology.

In addition to the listed controllers, the chemistry instrument 24 is provided with a power and communications interface 322 for all the modules included within it and with a flash lamp supply 324 that powers and operates the lamp within optical system 14. The power and communications interface 322 is operatively connected to the instrument CPU board 306 and to a suitable power supply 323 capable of providing the electrical power needed by the various motors and electronic components of the chemistry instrument 24.

METHOD OF OPERATION

Overview of Method

The method for operating the chemistry analyzer 24 basically entails a number of randomly selectable steps. Operation of the chemistry instrument 24 is timed about a repetitious sequence of cyclically transferring liquid from any selected container on the sample/reagent tray 15 to any selected cuvette 10 on the turntable 11, mixing liquids within the cuvettes on the turntable by turning it about the first axis, and rotating the turntable about the first axis.

The timing of these steps are graphically depicted in FIG. 25.

The operational cycles of all components are timed to a repetitious cycle of operation of turntable 11. The turntable 11 is held stationary by motor 12 for a period during which a disposable cuvettes 10 can be delivered to the turntable 11 by operation of the cuvette delivery module. This in turn displaces a spent cuvette, which is directed into a disposal container in the instrument. The turntable 11 is sequentially indexed to a stationary angular position about the first axis indicated at X—X (FIG. 13) with a selected cuvette 10 positioned at a cuvette access station A. It is then turned about the axis while mixing or centrifuging the contents of cuvettes 10 mounted to it.

An operator can add new cuvettes 10 to the chemistry instrument 24 at any time by initiating a Hopper access, which is manually entered at the keyboard 32 of workstation 30. When a cuvette insertion is requested, the instrument will position the cuvette magazine 75 of the cuvette delivery module 13 to locate an empty slot within it under the cartridge guide 102 and illuminate an indicator at the front of the chemistry instrument 24.

The operator can then insert a cartridge 40 filled with cuvettes 10. The chemistry instrument 24 will sense when the insertion has been completed as the cartridge 40 is withdrawn, and will proceed to the next empty slot. This is repeated until there are no more empty slots within the magazine 75 or until the operator terminates the process at keyboard 37. A pause indicator will be visible on monitor screen 31 until the cuvette insertion procedures have been completed.

As the contents of cuvettes 10 are being centrifuged within turntable 11, the step of analyzing their contents at a location adjacent to the turntable takes place within the optical system 14. The mechanically movable filter 205 is repositioned and data is transmitted from the optical testing module while turntable 11 is stationary.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so that the step of moving the pipette 18 provides randomly accessible transfer of liquid from any container on the tray to any cuvette on the turntable in the time in which the turntable 11 is stationary during each cycle of operation.

The method of sample delivery to chemistry instrument 24 involves the steps of receiving a manually placed draw tube 27 beneath a puncture tube 161, moving the draw tube between a lowered position wherein the draw tube is clear of the puncture tube and a raised position wherein the puncture tube forms a temporary opening through a closure on the draw tube, and subsequently inserting the pipette 18 coaxially through the opening in the closure to access the interior of the draw tube. It further comprises the step of detecting the level of liquid in the draw tube 27 as it is approached by the pipette 18, using the capacitive sensing system.

Where potentiometric tests are desired, the method further involves the steps of transferring a liquid sample from a container on the sample/reagent tray 15 positioned at the container access station C to ISE station E along the arcuate path of the pipette 18 and subsequent performance of potentiometric (ISE) tests on the sample.

Workstation 30 is also programmed to monitor operation of the chemistry instrument by detecting the level of liquid in each container on the sample/reagent tray 15 by capacitive sensing as it is approached by pipette 18, capturing information from indicia on containers on the tray 15 identifying the container and its contents, maintaining a current record of the amount of liquid in containers on the tray 15, and recording the elapsed time that has occurred since introduction of each sample into the chemical analyzer 24.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of providing an automated supply of cuvettes to a chemical analyzer, comprising the steps of:
    storing multiple upright stacks of cuvettes in a magazine, each stack of cuvettes including an exposed cuvette at its lower end;
    linearly moving the magazine to access the exposed cuvette at the lower end of a selected stack of cuvettes; and
    removing the exposed cuvette from the selected stack of cuvettes within the magazine; and
    inserting the exposed cuvette into an awaiting compartment within a turntable adapted to releasably mount a plurality of cuvettes.

2. The method of claim 1, further comprising the steps of:
    inserting the exposed cuvette into an awaiting compartment within a turntable adapted to releasably mount a plurality of cuvettes; and
    monitoring the selected stack of cuvettes to determine the number of cuvettes remaining in it.

3. The method of claim 1, further comprising the steps of:
    inserting the exposed cuvette into an awaiting compartment within a turntable adapted to releasably mount a plurality of cuvettes;
    simultaneously ejecting a used cuvette from the turntable as the exposed cuvette is inserted into the turntable; and
    monitoring the selected stack of cuvettes to determine the number of cuvettes remaining in it.

4. A cuvette delivery apparatus adapted to provide an automated supply of cuvettes to a chemical analyzer, comprising:
    magazine means including a plurality of upright slots for storing multiple stacks of cuvettes that are individually discharged at the lower end of each slot;
    drive means for imparting motion to the magazine means to provide access to a cuvette at the lower end of a selected stack of cuvettes; and
    dispenser means positioned adjacent the magazine means for removing a cuvette from the lower end of a selected stack of cuvettes within the magazine; and
    a turntable including spaced compartments rotatably mounted about a first axis operatively adjacent the magazine, the turntable being adapted to releasably mount a plurality of cuvettes within the spaced compartments; and said dispenser means further comprising a reciprocating ram adapted to engage and move the selected cuvette from the magazine means into one of the spaced compartments.

5. The cuvette delivery apparatus of claim 4, further comprising:
    a turntable rotatably mounted about a first axis operatively adjacent the magazine means, the turntable being adapted to releasably mount a plurality of cuvettes within spaced compartments.

6. A cuvette delivery apparatus adapted to provide an automated supply of cuvettes to a chemical analyzer, comprising:
    a magazine including spaced transverse walls defining a plurality of spaced upright slots between them, each slot holding a stack of cuvettes including an exposed cuvette at the lower end of the stack;
    a stationary wall positioned under the magazine the stationary wall being engaged by the exposed cuvette at the lower end of each stack;
    drive means for imparting longitudinal motion to the magazine to provide access to the exposed cuvette at the lower end of a selected stack of cuvettes; and
    discharge means recessed into the stationary wall for removing the exposed cuvette in a selected stack of cuvettes from within the magazine.

7. The cuvette delivery apparatus of claim 6, further comprising:
    a turntable rotatably mounted about a first axis operatively adjacent to the magazine, the turntable adapted to releasably mount a plurality of cuvettes within spaced, peripheral compartments; and
    power means operatively connected to the turntable for indexing the turntable at a stationary angular position about the first axis.

8. The cuvette delivery apparatus of claim 6, further comprising:
    a turntable rotatably mounted about a first axis operatively adjacent to the magazine, the turntable adapted to releasably mount a plurality of cuvettes within spaced, peripheral compartments;

power means operatively connected to the turntable for indexing the turntable at a stationary angular position about the first axis, the power means being further capable of rotating the turntable about the first axis to mix or centrifuge contents of cuvettes held within the turntable.

9. The cuvette delivery apparatus of claim 6, further comprising:

a turntable rotatably mounted about a first axis operatively adjacent to the magazine, the turntable adapted to releasably mount a plurality of cuvettes within spaced, peripheral compartments;

power means operatively connected to the turntable for indexing the turntable at a stationary angular position about the first axis;

the discharge means comprising a reciprocating ram positioned within a transverse slot formed across the fixed wall;

the exposed cuvette at the lower end of the selected stack of cuvettes being positioned within the transverse slot and being clear of the ram when the ram is in a retracted position; and actuator means for reciprocally moving the ram from the retracted position to an extended position by engaging and moving the exposed cuvette of the selected stack of cuvettes along the transverse slot for insertion into an awaiting compartment of the turntable.

10. The cuvette delivery apparatus of claim 6, further comprising:

a turntable including a plurality of angularly spaced, peripheral compartments rotatably mounted about a first axis adjacent to the magazine, the turntable being adapted to releasably mount a plurality of cuvettes within the compartments;

power means operatively connected to the turntable for indexing the turntable at a stationary angular position about the first axis;

the discharge means comprising a reciprocating ram positioned within a transverse slot formed across the fixed wall;

the exposed cuvette at the lower end of the selected stack of cuvettes being positioned within the transverse slot and being clear of the ram when the ram is in a retracted position;

actuator means for reciprocally moving the ram from the retracted position to an extended position by engaging and moving the exposed cuvette of the selected stack of cuvettes along the transverse slot for insertion into an awaiting compartment of the turntable; and follower means positioned at an upper end of the selected stack of cuvettes for monitoring the number of cuvettes remaining in the stack and inventorying the total number of cuvettes within the magazine.

11. The cuvette delivery apparatus of claim 6, further comprising:

a turntable including a plurality of angularly spaced, peripheral compartments rotatably mounted about a first axis adjacent to the magazine, the turntable being adapted to releasably mount a plurality of cuvettes within the compartments;

power means operatively connected to the turntable for indexing the turntable at a stationary angular position about the first axis;

the discharge means comprising a reciprocating ram positioned within a transverse slot formed across the fixed wall;

the exposed cuvette at the lower end of the selected stack of cuvettes being positioned within the transverse slot and being clear of the ram when the ram is in a retracted position;

actuator means for reciprocally moving the ram from the retracted position to an extended position by engaging and moving the exposed cuvette of the selected stack of cuvettes along the transverse slot for insertion into an awaiting compartment of the turntable; and follower means positioned at an upper end of the selected stack of cuvettes for monitoring the number of cuvettes remaining in the stack and inventorying the total number of cuvettes within the magazine;

a cuvette supply cartridge for holding a new stack of cuvettes for manual insertion into a selected one of the slots of the magazine; and stripper means adapted to be used in conjunction with the supply cartridge for permitting it to be inserted only into a selected slot that is empty, the stripper means further retaining the new stack of cuvettes within the selected slot while the cartridge is being removed.

12. A cuvette delivery apparatus adapted to provide an automated supply of cuvettes to a chemical analyzer, comprising:

a longitudinally elongated magazine including spaced transverse inner upright walls which define a plurality of spaced upright slots between the walls, each slot being adapted to hold an upright stack of cuvettes, each stack including an exposed cuvette at its lower end;

drive means for imparting longitudinal motion to the magazine to provide access to the exposed cuvette at the lower end of any selected one of the stacks of cuvettes;

a fixed planar surface under the magazine, the planar surface supporting the exposed cuvette at the lower end of each stack; and ram means positioned within a transverse slot formed across the planar surface for engaging and removing the exposed cuvette at the lower end of a selected stack of cuvettes from within the magazine.

13. The cuvette delivery apparatus of claim 12, further comprising:

a circular turntable including angularly spaced, peripheral compartments rotatably mounted about a first axis, the turntable being adapted to releasably mount a plurality of cuvettes within the compartments; and power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable.

14. The cuvette delivery apparatus of claim 12, further comprising:

a circular turntable including angularly spaced, peripheral compartments rotatably mounted about a first axis, the turntable being adapted to releasably mount a plurality of cuvettes within the compartments;

power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable;

the ram means comprising a reciprocating ram movable between a retracted position and an extended position within the transverse slot;

the exposed cuvette of the selected stack being positioned within the transverse slot in a position clear of the ram when the ram is in a retracted position; and actuator means for reciprocally moving the ram from the retracted position to an extended position by engaging and moving the exposed cuvette along the transverse slot for insertion into an awaiting compartment of the turntable.

15. The cuvette delivery apparatus of claim 12, further comprising:

a circular turntable including angularly spaced, peripheral compartments rotatably mounted about a first axis, the turntable being adapted to releasably mount a plurality of cuvettes within the compartments;

power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable;

the ram means comprising a reciprocating ram movable between a retracted position and an extended position within the transverse slot;

the exposed cuvette of the selected stack being positioned within the transverse slot in a position clear of the ram when the ram is in a retracted position;

actuator means for reciprocally moving the ram from the retracted position to an extended position by engaging and moving the exposed cuvette along the transverse slot for insertion into an awaiting compartment of the turntable; and follower means positioned on top of the selected stack of cuvettes for monitoring the number of cuvettes remaining in it and inventorying the total number of cuvettes within the magazine.

16. The cuvette delivery apparatus of claim 12, further comprising:

a circular turntable including angularly spaced, peripheral compartments rotatably mounted about a first axis, the turntable being adapted to releasably mount a plurality of cuvettes within the compartments;

power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable;

the ram means comprising a reciprocating ram movable between a retracted position and an extended position within the transverse slot;

the exposed cuvette of the selected stack being positioned within the transverse slot in a position clear of the ram when the ram is in a retracted position;

actuator means for reciprocally moving the ram from the retracted position to an extended position by engaging and moving the exposed cuvette along the transverse slot for insertion into an awaiting compartment of the turntable;

follower means positioned on top of the selected stack of cuvettes for monitoring the number of cuvettes remaining in it and inventorying the total number of cuvettes within the magazine; and the drive means further comprising:

a longitudinally oriented rack fixed to the magazine and meshing with a complementary drive gear.

17. The cuvette delivery apparatus of claim 12, further comprising:

a circular turntable including angularly spaced, peripheral compartments rotatably mounted about a first axis, the turntable being adapted to releasably mount a plurality of cuvettes within the compartments;

power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable;

the ram means comprising a reciprocating ram movable between a retracted position and an extended position within the transverse slot;

the exposed cuvette of the selected stack being positioned within the transverse slot in a position clear of the ram when the ram is in a retracted position;

actuator means for reciprocally moving the ram from the retracted position to an extended position by engaging and moving the exposed cuvette along the transverse slot for insertion into an awaiting compartment of the turntable;

follower means positioned on top of the selected stack of cuvettes for monitoring the number of cuvettes remaining in it and inventorying the total number of cuvettes within the magazine;

the drive means further comprising:

a longitudinally oriented rack fixed to the magazine and meshing with a complementary drive gear;

an indexing strip fixed to the magazine; and sensing means for reading the strip to determine the longitudinal position of the magazine.

18. The cuvette delivery apparatus of claim 12, further comprising:

a circular turntable including angularly spaced, peripheral compartments rotatably mounted about a first axis, the turntable being adapted to releasably mount a plurality of cuvettes within the compartments;

power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable;

the ram means comprising a reciprocating ram movable between a retracted position and an extended position within the transverse slot;

the exposed cuvette of the selected stack being positioned within the transverse slot in a position clear of the ram when the ram is in a retracted position;

actuator means for reciprocally moving the ram from the retracted position to an extended position by engaging and moving the exposed cuvette along the transverse slot for insertion into an awaiting compartment of the turntable;

follower means positioned on top of the selected stack of cuvettes for monitoring the number of cuvettes remaining in it and inventorying the total number of cuvettes within the magazine;

the drive means further comprising:

a longitudinally oriented rack fixed to the magazine and meshing with a complementary drive gear;

an indexing strip fixed to the magazine;

sensing means for reading the strip to determine the longitudinal position of the magazine; and a cuvette supply cartridge for holding a new stack of cuvettes for manual insertion into one of the slots of the magazine.

19. The cuvette delivery apparatus of claim 12, further comprising:

a circular turntable including angularly spaced, peripheral compartments rotatably mounted about a first axis, the turntable being adapted to releasably mount a plurality of cuvettes within the compartments;

power means operatively connected to the turntable for positioning the turntable at a stationary angular position about the first axis to allow insertion of the exposed cuvette from the selected stack into a predetermined compartment of the turntable and for rotating the turntable about the first axis to mix or centrifuge contents of cuvettes held within the turntable;

the ram means comprising a reciprocating ram movable between a retracted position and an extended position within the transverse slot;

the exposed cuvette of the selected stack being positioned within the transverse slot in a position clear of the ram when the ram is in a retracted position;

actuator means for reciprocally moving the ram from the retracted position to an extended position by engaging and moving the exposed cuvette along the transverse slot for insertion into an awaiting compartment of the turntable;

follower means positioned on top of the selected stack of cuvettes for monitoring the number of cuvettes remaining in it and inventorying the total number of cuvettes within the magazine;

the drive means further comprising:

a longitudinally oriented rack fixed to the magazine and meshing with a complementary drive gear;

an indexing strip fixed to the magazine;

sensing means for reading the strip to determine the longitudinal position of the magazine;

a cuvette supply cartridge for holding a new stack of cuvettes for manual insertion into one of the slots of the magazine; and stripper means adapted to be used in conjunction with the supply cartridge for permitting the supply cartridge to be inserted only into an empty slot of the magazine, the stripper means retaining the new stack of cuvettes within the empty slot while the cartridge is being removed.

20. A cuvette delivery apparatus adapted to provide an automated supply of cuvettes to a chemical analyzer, comprising:

an elongated magazine including spaced transverse inner upright walls defining a plurality of spaced upright slots between the walls, each slot being adapted to hold an upright stack of cuvettes including an exposed cuvette at its lower end;

fixed guide rods supporting the magazine for longitudinal movement of the magazine relative to the rods;

a rack fixed to the magazine and engagable by a complementary drive gear for imparting longitudinal motion to the magazine to provide access to the exposed cuvette at the lower end of any selected one of the stacks of cuvettes;

a fixed planar surface supporting the exposed cuvettes at the lower ends of the respective slots within the magazine;

a reciprocating ram riding in a transverse slot formed across the planar surface for engaging and separating the exposed cuvette from the lower end of the selected stack of cuvettes within the magazine;

a circular turntable including angularly spaced, peripheral compartments rotatably mounted the about a first axis, the turntable being adapted to releasably mount a plurality of cuvettes within the compartments;

power means operatively connected to the turntable for positioning the turntable at a stationary angular position about the first axis to allow insertion of the exposed cuvette from the lower end of a selected stack of cuvettes within the magazine into a predetermined compartment of the turntable and for alternatively rotating the turntable about the first axis to mix or centrifuge contents of cuvettes held within the turntable;

the exposed cuvette at the lower end of the selected stack being positioned within the transverse slot and being clear of the ram when the ram is in a retracted position;

actuator means for reciprocally moving the ram from the retracted position to an extended position by engaging and moving the exposed cuvette of the selected stack along the transverse slot for insertion into an awaiting compartment of the turntable; and follower means positioned on top of the selected stack of cuvettes within the magazine for monitoring the number of cuvettes remaining in the selected stack and inventorying the total number of cuvettes within the magazine.

* * * * *